US012274769B2

(12) United States Patent
Kelly et al.

(10) Patent No.: US 12,274,769 B2
(45) Date of Patent: Apr. 15, 2025

(54) SKINCARE COMPOSITIONS

(71) Applicant: THE BOOTS COMPANY PLC, Nottingham (GB)

(72) Inventors: Matthew Kelly, Ockbrook (GB); Julian Cocking, Nottingham (GB); Helen Sisson, Nottingham (GB)

(73) Assignee: THE BOOTS COMPANY PLC, Nottingham (GB)

( * ) Notice: Subject to any disclaimer, the term of this patent is extended or adjusted under 35 U.S.C. 154(b) by 486 days.

(21) Appl. No.: 17/621,930

(22) PCT Filed: Jul. 23, 2020

(86) PCT No.: PCT/EP2020/025342
§ 371 (c)(1),
(2) Date: Dec. 22, 2021

(87) PCT Pub. No.: WO2021/013384
PCT Pub. Date: Jan. 28, 2021

(65) Prior Publication Data
US 2022/0273529 A1    Sep. 1, 2022

(30) Foreign Application Priority Data

Jul. 24, 2019    (EP) .................................... 19020443

(51) Int. Cl.
*A61K 8/42*        (2006.01)
*A45D 40/00*    (2006.01)
(Continued)

(52) U.S. Cl.
CPC ............ *A61K 8/0237* (2013.01); *A61K 8/064* (2013.01); *A61K 8/34* (2013.01); *A61K 8/42* (2013.01);
(Continued)

(58) Field of Classification Search
USPC ......................................................... 424/401
See application file for complete search history.

(56) References Cited

U.S. PATENT DOCUMENTS

| 4,335,103 A | 6/1982 | Barker et al. |
| 2007/0014823 A1 | 1/2007 | Iwata |

FOREIGN PATENT DOCUMENTS

| CN | 101080252 A | 11/2007 |
| CN | 101394899 A | 3/2009 |

(Continued)

OTHER PUBLICATIONS

International Application No. PCT/EP2020/025342, International Search Report and Written Opinion, mailed Oct. 29, 2020.

(Continued)

*Primary Examiner* — Kyung S Chang
(74) *Attorney, Agent, or Firm* — MARSHALL, GERSTEIN & BORUN LLP

(57) ABSTRACT

According to the present invention there is provided a multi-phase, fluid skincare composition comprising (a) at least one cream phase; and (b) at least one gel phase; wherein the cream phase and the gel phase are visually distinct phases that are packaged in physical contact; wherein the viscosity ratio of the cream phase to the gel phase is 1.25 or greater:1 or 1:1.25 or greater, preferably 1.25 or greater:1; wherein the viscosity of the cream phase is at least 15 Pa-s; wherein the viscosity of the gel phase is at least 10 Pa-s; wherein the cream phase and the gel phase are present in the composition at a level such that the weight ratio of cream phase to the gel phase is within the range of from 65:35 to 35:65; and wherein the viscosity is measured at 23° C. The present invention also provides a collapsible tube having an outlet bore and containing the composition as defined above, wherein the tube is filled such that, when the composition is extended from the outlet bore, the extruded (Continued)

composition comprises the cream phase and the gel phase that are visually distinct from one another and within a weight ratio of the cream phase to the gel phase of between 65:35 and 35:65 across the cross-section of the extrusion. The present invention also provides a use of the composition defined above for the purpose of one or more of moisturising the skin, including hydrating the skin, improving the radiance of the skin, improving skin suppleness, reducing skin tightness, nourishing skin and/or reducing dryness. The present invention also provides a use of the composition defined above for the purpose of topical application to any one or more of the face, the neck skin and/or the decollete, preferably the face.

8 Claims, 13 Drawing Sheets

(51) Int. Cl.
| | | |
|---|---|---|
| *A61K 8/02* | (2006.01) | |
| *A61K 8/06* | (2006.01) | |
| *A61K 8/34* | (2006.01) | |
| *A61K 8/73* | (2006.01) | |
| *A61K 8/92* | (2006.01) | |
| *A61Q 19/00* | (2006.01) | |

(52) U.S. Cl.
CPC ............... *A61K 8/735* (2013.01); *A61K 8/92* (2013.01); *A61Q 19/007* (2013.01); *A45D 40/00* (2013.01); *A45D 2200/05* (2013.01); *A61K 2800/87* (2013.01)

(56) References Cited

FOREIGN PATENT DOCUMENTS

| | | |
|---|---|---|
| FR | 2925302 A1 | 6/2009 |
| FR | 2932980 A1 | 1/2010 |
| WO | WO-2004/047783 A1 | 6/2004 |
| WO | WO-2007/004200 A1 | 1/2007 |
| WO | WO-2007/007279 A2 | 1/2007 |
| WO | WO-2007/029152 A2 | 3/2007 |
| WO | WO-2007/029153 A2 | 3/2007 |
| WO | WO-2007/029154 A2 | 3/2007 |
| WO | WO-2009/053898 A2 | 4/2009 |
| WO | WO-2018/003793 A1 | 1/2018 |

OTHER PUBLICATIONS

European Patent Application No. 19020443.8, Extended European Search Report, dated Jan. 31, 2020.
International Application No. PCT/EP2020/025342, International Preliminary Report on Patentability, dated Sep. 16, 2021.

|  | Transit Duration (hours) | | |
|---|---|---|---|
|  | 0.5 | 2 | 8 |
| Product A | | | |
| Product B | | | |
| Product C | | | |

FIGURE 4

SKINCARE COMPOSITIONS

CROSS REFERENCE TO RELATED APPLICATIONS

This application is the U.S. national phase of PCT Application No. PCT/EP2020/025342, filed Jul. 23, 2020, which claims priority to European Application No. 19020443.8, filed Jul. 24, 2019, the entire disclosures of which are hereby incorporated by reference in their entirety.

FIELD OF THE INVENTION

The present invention relates to a multi-phase, fluid skincare composition comprising a cream phase and a gel phase that are visually distinct and of varying viscosities, whereby the visually distinct pattern of the two phases is stable during transit and during dispensing.

BACKGROUND TO THE INVENTION

One common issue when formulating skincare compositions is how to combine ingredients that are incompatible. Whilst such an issue can be solved through packaging comprising separate chambers in order to keep the incompatible ingredients separate, such packaging can be difficult to manufacture, generally require more raw packaging material that can have an environmental impact and do not always deliver the composition in a manner that is desirable to the consumer.

Another solution to this problem is to develop multi-phase compositions, whereby one incompatible ingredient forms part of one phase and the other incompatible ingredient forms part of a further visually distinct phase. However, one issue with multi-phase compositions when fluid, especially when the phases forming the composition have varying rheological profiles (such as varying viscosities), is that one phase may flow more freely than another phase, meaning that, over time (either under static conditions or with movement) one phase may move in relation to another phase within a container. For example, with respect to a multi-phase composition within a jar, a more freely flowing phase may, over time, move below a less freely flowing phase. This causes problems when the consumer wishes to obtain a consistent proportion of the phases from a package with each use. This moving of one phase against another is more problematic when the multi-phase composition is made up of a cream phase and a gel phase (compared to two gel phases or two cream phases) as there is generally increased surface tension where the hydrophobic cream phase meets the hydrophilic gel phase and this increases the likelihood of one phase sliding against the other phase.

In the prior art, this issue is generally dealt with by matching the rheological profiles, in particular the viscosities, of the phases making up a composition, and this is discussed in, for example, Chinese patent publication CN101394899, International patent publications WO201803793 and WO2004047783 and French patent application FR2925302. However, it is not always possible to match the viscosities of the phases of a composition. For example, increasing the viscosity of a phase for matching purposes may make the composition more prone to pilling on the skin. Also altering the viscosities of one or more phases could have a detrimental impact on the skin-feel of the multi-phase composition upon application.

French patent application FR2932980 relates to a cosmetic composition in the form of a stick, said stick being formed of a liquid core comprising at least one fatty phase that is liquid at ambient temperature and retained inside a solid sheath comprising at least one solid fat substance at ambient temperature. Whilst this multi-phase composition is made up of two phase with very different rheological profiles, this overall skincare composition is not fluid.

International patent publications WO2007029153, WO2007029154 and WO2007029152 and Chinese patent publication CN101080252 relate to solid multi-phase skincare compositions. Whilst varying viscosities are discussed in these publications, these skincare compositions are not fluid.

International patent publication WO2007007279 relates to multiphase compositions comprising two or more gel phases.

There remains a need for fluid multi-phase compositions comprising visually distinct phases where the visually distinct pattern of the two phases is stable during transit and during dispensing.

SUMMARY OF THE INVENTION

Without wishing to be bound by theory, in a similar way that oil and water phases separate in the absence of an emulsifier, the oil and/or silicone component of the cream phase of the present invention repels the gel phase of the present invention, forming surface tension between the two phases. This surface tension is particularly prominent when the cream phase is in the form of a water-in-oil and/or silicone emulsion (i.e. when the oil and/or silicone that repels the aqueous gel phase forms the continuous phase of the cream). Whilst this is beneficial in terms of preventing the two phases from mixing when packaged adjacent to one another, this means that one phase is more likely to be able to flow independently of the other phase, particularly when the phases are of differing viscosities. When one phase is able to flow independently of the other phase, this can lead to one phase moving to a different position in relation to the other phase either when the packaging is stationary (i.e. under the influence of gravity alone) or when the packaging is being transported (where kinetic energy has a role to play also), and this can ultimately lead to a consumer obtaining highly varying proportions of the cream and gel phase when the multi-phase composition is being dispensed from the packaging.

The inventors have surprisingly demonstrated that the proportions of the cream phase and the gel phase of a multi-phase composition is critical to the stability of the visually distinct pattern of the two phases. In particular, it is important that the phases are present in the composition at a level such that the weight ratio of the cream phase to the gel phase is within the range of from 65:35 to 35:65.

Thus, in one aspect the present invention provides a multi-phase, fluid skincare composition comprising: (a) at least one cream phase; and (b) at least one gel phase; wherein the cream phase and the gel phase are visually distinct phases that are packaged in physical contact; wherein the viscosity ratio of the cream phase to the gel phase is 1.25 or greater:1 or 1:1.25 or greater, preferably 1.25 or greater:1; wherein the viscosity of the cream phase is at least 15 Pa·s; wherein the viscosity of the gel phase is at least 10 Pa·s; wherein the cream phase and the gel phase are present in the composition at a level such that the weight ratio of cream phase to the gel phase is within the range of from 65:35 to 35:65; and wherein the viscosity is measured at 23° C.

In one embodiment, the viscosity ratio of the cream phase to the gel phase in the fluid skincare composition of the present invention is 1.3 or greater:1 or 1:1.3 or greater, preferably 1.35 or greater:1 or 1:1.35 or greater, more preferably 1.4 or greater:1 or 1:1.4 or greater:1. In a further embodiment, the viscosity ratio of the cream phase to the gel phase in the fluid skincare composition of the present invention is 1.3 or greater:1, preferably 1.35 or greater:1, more preferably 1.4 or greater:1.

In one embodiment, the viscosity ratio of the cream phase to the gel phase in the fluid skincare composition of the present invention is from 1:3 to 3:1, preferably from 1:2.8 to 2.8:1, more preferably from 1:2.5 to 2.5:1, more preferably from 1:2.2 to 2.2:1.

In one embodiment, the viscosity of the cream phase in the fluid skincare composition of the present invention is at least 18 Pa·s, preferably at least 25 Pa·s, more preferably at least 32 Pa·s, more preferably at least 40 Pa·s, wherein the viscosity is measured at 23° C. In one embodiment, the viscosity of the gel phase in the fluid skincare composition of the present invention is at least 12 Pa·s, preferably at least 14 Pa·s, more preferably at least 16 Pa·s, more preferably at least 18 Pa·s, more preferably at least 20 Pa·s, wherein the viscosity is measured at 23° C.

In one embodiment, the cream phase and the gel phase are present in the fluid skincare composition of the present invention at a level such that the weight ratio of the cream phase to the gel phase is within the range of from 60:40 to 40:60, preferably from 58:42 to 42:58, more preferably from 56:44 to 44:56, more preferably from 54:46 to 46:54, more preferably from 52:48 to 48:52.

In one embodiment, the cream phase in the fluid skincare composition of the present invention is in the form of a water-in-oil and/or silicone emulsion, preferably a water-in-oil emulsion.

In one embodiment, the fluid skincare composition of the present invention comprises a bitter substance. In a preferred embodiment, the bitter substance is chosen from denatonium compounds, aromatic oils, preferably peppermint oil, *eucalyptus* oil, bitter almond oil, menthol, fruit aroma substances, preferably aroma substances from lemons, oranges, limes, grapefruit or mixtures thereof, preferably denatonium compounds.

In a further aspect, the present invention provides a collapsible tube having an outlet bore and containing the fluid skincare composition as defined above, wherein the tube is filled such that, when the composition is extruded from the outlet bore, the extruded composition comprises the cream phase and the gel phase that are visually distinct from one another and within a weight ratio of the cream phase to the gel phase of between 65:35 and 35:65 across the cross-section of the extrusion. In a preferred embodiment, the collapsible tube is filled such that, when the composition is extruded from the outlet bore, the extruded composition comprises the cream phase and the gel phase that are visually distinct from one another and within a weight ratio of the cream phase to the gel phase of between 60:40 and 40:60, preferably between 58:42 and 42:58, more preferably between 56:44 and 44:56, more preferably between 54:46 and 46:54, more preferably between 52:48 and 48:52, across the cross-section of the extrusion. In a further embodiment, the collapsible tube is filled such that, when the composition is extruded from the outlet, the composition forms a visually distinct pattern selected from the following list: striped, marbled, check, mottled, veined, speckled, ribbons, helical, grooved, ridged, waved, sinusoidal, spiral, contoured, weave or woven, such as basket weave and combinations thereof.

In a further aspect, the present invention provides a use of the fluid skincare composition defined above for the purpose of one or more of moisturising the skin, including hydrating the skin, improving the radiance of the skin, improving skin suppleness, reducing skin tightness, nourishing skin and/or reducing dryness.

In a further aspect, the present invention provides a use of the fluid skincare composition defined above for the purpose of topical application to any one or more of the face, the neck skin and/or the décolleté, preferably the face.

DETAILED DESCRIPTION OF THE INVENTION

All percentages, parts and ratios are based upon the total weight of the compositions of the present invention, unless otherwise specified. The term "weight percent" may be denoted as "wt %" herein.

Herein, "comprising" means that other step and other ingredients which do not affect the end results can be added. This term encompasses the term "consisting of".

In the present application, the term "about" or "approximately" or "around" may encompass ±10%, such as ±5%, for example ±2%, preferably ±1%.

Multi-Phase

The present invention relates to multi-phase compositions. The multi-phase composition comprises (a) at least one cream phase and (b) at least one gel phase. The cream phase and the gel phase are visually distinct phases that are packaged in physical contact with one another.

By the term "multi-phased" or "multi-phase" as used herein, it is meant that at least a cream phase and a gel phase occupy separate and distinct physical spaces inside the package in which they are stored, but are in direct contact with one another (i.e. they are not separated by a barrier and they are not emulsified). Within the multi-phase composition, the cream phase and the gel phase are present as a visually distinct pattern. The pattern results from making the cream phase and the gel phase separately and then mixing the phases of the multi-phase composition together. The patterns include but are not limited to the following examples: striped, marbled, check, mottled, veined, speckled, ribbons, helical, grooved, ridged, waved, sinusoidal, spiral, contoured, weave or woven (such as basket weave) and combinations thereof. Preferably the pattern is selected from the group consisting of striped, spiral, marbled and combinations thereof. In a preferred embodiment the striped pattern may be relatively uniform and even across the dimension of the package, so that, when the composition is dispensed from the package, a consistent proportion of the phases is obtained. The phases may be of various different colours, or include particles, glitter or pearlescence so that the phases are visually distinct.

The multi-phase composition of the present invention can contain further phases in addition to the at least one cream phase and the at least one gel phase. When the multi-phase compositions contain such additional phases, these phases are preferably visually distinct phase that are packaged in physical contact with at least either the cream phase or the gel phase. It is preferred in the present invention that such additional phases also have the properties which are required of either the cream phase or the gel phase in relation to, for example, the viscosity.

Visually Distinct

By the term "visually distinct" as used herein, it is meant that the regions occupied by each phase can be separately seen by the human eye as distinctly separate regions in contact with one another (i.e. they are not emulsions or dispersions of particles of about 100 μm or less).

Skincare Composition

The term "skincare composition" as used herein, refers to compositions of the present invention, wherein the compositions are intended to include only those compositions for topical application to the skin, preferably face (including lips) neck and décolletage. The term specifically excludes those compositions that are directed primarily to other applications such as oral care (including compositions in the form of a toothpaste, tooth gel, dentifrice, prophy paste, mouthwash, rinse or tooth mousse), hard surface cleansing, fabric or laundry cleansing, and similar other application not intended primarily for topical application to the skin.

Fluid

The term "fluid" is understood to mean, according to the invention, a composition which flows out through an orifice of, for example, a tube when an extrusion pressure is applied, at ambient temperature, but does not flow under its own weight. Thus, the term "fluid" does not cover solid compositions that cannot be extruded from an orifice. Typical orifice sizes range from 2 mm to 10 mm in diameter, preferably 3 mm to 8 mm in diameter, more preferably 4 to 6 mm in diameter. The extrusion stress necessary to extrude the composition through the orifice should be such that it can be carried out straightforwardly by a human hand. In one embodiment, the extrusion stress necessary to extrude the composition is between 20 and 500 Pascal (Pa), preferably between 30 and 400 Pa, more preferably between 40 and 300 Pa.

In order to obtain these flow properties, the compositions of the present invention would typically be formulated so as to be shear thinning Shear thinning means that the viscosity of the composition would decrease under shear stress (i.e. the viscosity of the composition would decrease when pressure, such as pressing of a collapsible tube packaging, is applied). Compositions that exhibit shear thinning are preferable. In such circumstances, below a yield stress, a composition would preferably show solid-like behaviour (i.e. not flow). Once a minimum level of shear stress is applied, the viscosity of the composition decreases and thus the composition shows liquid-like, flowing behaviour. The skilled person would readily know how to formulate a composition so that it exhibits shear thinning, and in this regard extensive research has been carried out in relation to optimizing the shear-thinning properties of cosmetics and of toothpastes. With this in mind, any discussions regarding viscosity values herein relate to when the phases or composition are at rest.

The skincare composition of the present invention has a viscosity of at least 10 Pascal seconds (Pa·s). In one embodiment the composition has a viscosity of at least 13 Pa·s. In a further embodiment the composition has a viscosity of at least 16 Pa·s. In a further embodiment the composition has a viscosity of at least 19 Pa·s. In a further embodiment the composition has a viscosity of at least 22 Pa·s.

In one embodiment the skincare composition of the present invention has a viscosity of less than 200 Pa·s. In a further embodiment the skincare composition has a viscosity of less than 180 Pa·s. In a further embodiment the skincare composition has a viscosity of less than 160 Pa·s.

Viscosity is a measure of its resistance to gradual deformation by shear stress or tensile stress, where a liquid with a greater viscosity has a greater resistance to gradual deformation (and in an informal sense is "thicker") than a liquid with a lesser viscosity. The skilled person would be well aware of how to determine the viscosity of a given liquid. A suitable method for measuring viscosity is presented in Example 2, in particular using a Brookfield RVDV-I Prime viscometer with a heliopath, a speed of 10 revolutions per minute (rpm) for a time of 30 seconds using a T Bar spindle. In all of the embodiments discussed above, viscosity is measured at 23° C.

The spindle of the viscometer can affect the viscosity measurements. In order to ensure that the viscosity readings between the cream phase and the gel phase are comparable, it was first determined which T bar spindle could achieve a similar initial torque reading. It was determined, with respect to the cream phase of Table 1, that a TBar Spindle C (otherwise known as spindle 93) was the most suitable spindle. It was determined, with respect to the gel phase of Table 2, that a TBar Spindle B (otherwise known as spindle 92) was the most suitable spindle. The skilled person would be well aware of how to select the correct TBar spindle in order to achieve comparable initial torque readings. All other viscosity measurement parameters (temperature, viscometer model, spindle rotation speed, test time period, etc.) remained unchanged when testing the viscosity of the cream and gel phases.

Cream Phase

The term "cream phase" is understood to mean, according to the invention, thick (i.e. viscous) emulsions of oil and/or silicone with water. The International Union of Pure and Applied Chemistry (IUPAC) definition of an emulsion is a fluid system in which liquid droplets are dispersed in a liquid. It is preferable for the cream phase of the present invention to be a water-in-oil (and/or silicone) emulsion which is composed of small droplets of water dispersed in a continuous oil (and/or silicone) phase, rather than an oil (and/or silicone)-in-water emulsion which is composed of small droplets of oil and/or silicone dispersed in a continuous water phase. This is because in a water-in-oil (and/or silicone) emulsion the oil and/or silicone forms the outer surface of the emulsion, and as this oil and/or silicone is not miscible with the gel phase, the cream and gel phases are better able to remain as separate phases within the multiphase composition. The cream may also be in the form of a multiple emulsion, for example water-in-oil and/or silicone-in-water or oil and/or silicone-in-water-in-oil and/or silicone, and, for the reasons discussed above, a oil and/or silicone-in-water-in-oil and/or silicone emulsion is more preferable. In one embodiment, the emulsion is a water-in-oil emulsion. In one embodiment of the present invention the aqueous phase is present at a concentration of between 50% and 90%, preferably between 60% and 85%, more preferably between 65% and 80%.

The emulsion may comprise an organic oil. The organic oil may be volatile or non-volatile. The organic oil may include a diluent, a solvent, a polyolefin polymer, an ester oil or combination thereof.

The term "ester oil" means an oil that is liquid at room temperature (23° C.) comprising at least one ester functional group. The ester oil used herein is chosen, for example, from monoesters.

The ester oil may, for example, be chosen from the monoesters of formula $R_1COOR_2$ wherein $R_1$ may be selected from linear, branched or aromatic (preferably aromatic) hydrocarbon-based chains comprising from 3 to 10, or 4 to 9, or 5 to 8 carbon atoms and $R_2$ may be chosen from linear or branched hydrocarbon-based chains comprising from 3 to 40 carbon atoms, such as from 7 to 30 carbon atoms and further such as from 10 to 20 carbon atoms. $R_1$ and/or $R_2$ may be substituted with, for example, hydroxyl groups.

Examples of the ester oils that may be mentioned include benzoates such as alcohol benzoates or alkyl benzoates, isodecyl neopentanoate; isocetyl octanoate; isononyl isononanoate, isodecyl isononanoate, tridecyl isononanoate; hexyl laurate, 2-hexyldecyl laurate; isopropyl myristate, isocetyl myristate, isotridecyl myristate, 2 octyldodecyl myristate; isopropyl palmitate, 2-ethylhexyl palmitate, isooctyl palmitate, isocetyl palmitate, isodecyl palmitate, isostearyl palmitate, 2-octyldecyl palmitate; isopropyl isostearate, 2-octyldodecyl stearate, isostearyl isostearate and 2-octyldodecyl erucate.

In one embodiment, the aqueous component of the cream phase has a pH of between 2 and 8.5, preferably between 3 and 7.5, more preferably between 3.5 and 6.5.

Emulsifiers

The compositions of the present invention may optionally comprise an emulsifier. The emulsifier helps disperse and suspend an aqueous water phase within an oil phase or vice versa. Suitable emulsifiers include all those suitable for the purpose and known by those skilled in the art for use in skin care products. Preferably these emulsifiers have an HLB (hydrophile-lipophile balance) value of or less than 14, more preferably from 2 to 14 and still more preferably from 4 to 14. The HLB is known in the art to be an empirical expression for the relationship of the hydrophilic and hydrophobic groups of an emulsifier or a surfactant, where a higher HLB value indicates a more water-soluble emulsifier or surfactant.

A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains and chains comprising moieties derived from both ethylene oxide and propylene oxide. Other examples include alkyl-modified dimethicone copolyols, in other words compounds which comprise $C_2$-$C_{30}$ pendant side chains. Still other useful dimethicone copolyols include materials having various cationic, anionic, amphoteric and zwitterionic pendant moieties.

Emulsifiers also include various non-ionic and anionic emulsifying agents such as sugar esters and polyesters, alkoxylated sugar esters and polyesters, $C_1$-$C_{30}$ fatty acid esters of $C_1$-$C_{30}$ fatty alcohols, alkoxylated derivatives of $C_1$-$C_{30}$ fatty acid esters of $C_1$-$C_{30}$ fatty alcohols, alkoxylated ethers of $C_1$-$C_{30}$ fatty alcohols, polyglyceryl esters of $C_1$-$C_{30}$ fatty acids, $C_1$-$C_{30}$ esters of polyols, $C_1$-$C_{30}$ ethers of polyols, alkyl phosphates, polyoxyalkylene fatty ether phosphates, fatty acid amides, acyl lactylates, soaps and mixtures thereof. Non-limiting preferred examples of these non-silicon-comprising emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate and mixtures thereof.

Alternatively the emulsifiers include various cationic emulsifying agents. Cationic emulsifying agents that are particularly effective for skincare include dialkyl quaternary compounds, such as distearyldimonium chloride, amidoamine quaternary compounds such as palmitamidopropyltrimonium chloride, or a mixture thereof.

Alternatively the emulsifiers include various polymeric emulsifying agents. Such agents form structured interfacial films that prevent the coalescence of oil drops. The polymeric emulsifying agent may be in the form of a linear block, graft or star polymer. Many viscosity-controlling agents, such as carbomers and hydroxypropyl methylcellulose, can be used as polymeric emulsifiers. Preferably the polymeric emulsifying agent is in the form of high molecular weight polyacrylic acid polymers, such as Pemulen™ from Lubrizol, an acrylates/$C_{10}$-$C_{30}$ alkyl acrylate crosspolymer, crosslinked with allyl pentaerythritol.

In embodiments where one or more emulsifiers are present in the cosmetic composition, the one or more emulsifiers may be present at a concentration between about 0.01 wt % and about 8 wt %. Preferably the one or more emulsifiers are present at a concentration between about 0.05 wt % and about 5 wt %. More preferably the one or more emulsifiers are present at a concentration between about 0.1 wt % and about 3 wt %. These concentration ranges relate to the cream phase specifically.

Surfactants

The composition of the present invention may further comprise one or more surfactants, including but not limited to, anionic surfactants (for example sodium lauryl sulphate, sodium laureth sulphate, ammonium laureth sulphate, disodium laureth sulfosuccinate and sodium $C_{12-15}$ pareth-12 carboxylate), amphoteric/zwitterionic surfactants (for example cocamidopropyl betaine, sodium cocoamphoacetate and cocamidopropyl hydroxysultaine), non-ionic surfactants (for example cocamide DEA, cocamide MEA, decyl glucoside, lauryl glucoside), cationic surfactants (for example cetrimonium chloride, behentrimonium chloride and benzalkonium chloride) and mixtures thereof.

In embodiments where one or more surfactants are present in the cosmetic composition, the one or more surfactants may be present at a concentration between about 0.1 wt % and about 10 wt %. Preferably the one or more surfactants are present at a concentration between about 0.25 wt % and about 7.5 wt %. More preferably the one or more surfactants are present at a concentration between about 0.5 wt % and about 6 wt %. More preferably the one or more surfactants are present at a concentration between about 0.5 wt % and about 5 wt %. These concentration ranges relate to the cream phase specifically.

Gel Phase

The term "gel phase" is understood to mean, according to the present invention, a substantially dilute cross-linked systems which exhibit no flow under its own weight in a steady-state. Gels comprise liquids dispersed within a cross-linked system. The gel phase comprises a gelling agent in order to form this cross-linked system. The gels of the present invention are aqueous (i.e. the gels of the present invention comprise an aqueous base).

Gelling Agent

For the purposes of the present invention, the term "gelling agent" means a compound that is capable of gelling the gel phase according to the invention.

The gelling agents are preferably non-emulsifying; preferably, they do not contain any fatty chains such as alkyl chains greater than $C_7$ and especially ranging from $C_7$ to $C_{24}$.

The gelling agent may be chosen from synthetic polymeric gelling agents, mixed silicates and fumed silicas, polymeric gelling agents which are natural or of natural origin, especially polysaccharides and mixtures thereof.

For the purposes of the invention, the term "of natural origin" is intended to denote polymeric gelling agents obtained by modification of natural polymeric gelling agents. These gelling agents may be particulate or non-particulate. More specifically, these gelling agents fall within the category of polysaccharides. In general, the non-starchy polysaccharides may be chosen from polysaccharides produced by microorganisms; polysaccharides isolated from algae and higher plant polysaccharides, such as homogeneous polysaccharides, in particular celluloses and derivatives thereof or fructosans, heterogeneous polysaccharides such as gum arabics, galactomannans, glucomannans and pectins and derivatives thereof; and mixtures thereof.

In particular, the polysaccharides may be chosen from biopolysaccharide gums of microbial origin, in particular xanthan gums or scleroglucan, fructans, gellans, glucans, glycogen, pullulan, dextrans, celluloses and derivatives thereof, in particular methylcelluloses, hydroxyalkylcelluloses, ethylhydroxyethylcelluloses and carboxymethylcelluloses, mannans, xylans, lignins, arabans, galactans, galacturonans, alginate-based compounds, chitin, chitosans, glucuronoxylans, arabinoxylans, xyloglucans, glucomannans, pectic acids and pectins, arabinogalactans, carrageenans, agars, glycosaminoglucans, gum arabics, tragacanth gums, ghatti gums, karaya gums, locust bean gums, galactomannans such as guar gums and nonionic derivatives thereof, in particular hydroxypropyl guar and ionic derivatives thereof, mucopolysaccharides, and in particular chondroitin sulfates and mixtures thereof. Preferably the polysaccharide is a biopolysaccharide gums of microbial origin, preferably xanthan gum. These polysaccharides may be chemically modified, especially with urea or urethane groups or by hydrolysis, oxidation, esterification, etherification, sulfatation, phosphatation, amination, amidation or $C_1$-$C_6$ alkylation reaction, or by several of these modifications. The derivatives obtained may be anionic, cationic, amphoteric or nonionic. The polysaccharides may be chosen from carrageenans, in particular kappa carrageenan, gellan gum, agar-agar, xanthan gum, alginates-based compounds, in particular sodium alginate, scleroglucan gum, guar gum, inulin and pullulan and mixtures thereof. Such a gelling agent may be used in a proportion of from 0.1 wt % to 8 wt % relative to the total weight of the gel phase, especially from 0.1 wt % to 6 wt % and preferably between 0.5 wt % and 2.5 wt % relative to the total weight of the gel phase.

More precisely, these polysaccharides that are suitable for use in the invention may be distinguished according to whether they are derived from microorganisms, from algae or from higher plants, and are detailed below.

Xanthan gum is a heteropolysaccharide produced at the industrial scale by the aerobic fermentation of the bacterium *Xanthomonas campestris*. Its structure consists of a main chain of β(1,4)-linked β-D-glucoses, similar to cellulose. One glucose molecule in two bears a trisaccharide side chain composed of an α-D-mannose, a β-D-glucuronic acid and a terminal β-D-mannose. The internal mannose residue is generally acetylated on carbon 6. About 30% of the terminal mannose residues bear a pyruvate group linked in chelated form between carbons 4 and 6. The charged pyruvic acids and glucuronic acids are ionizable, and are thus responsible for the anionic nature of xanthan (negative charge down to a pH equal to 1). The content of pyruvate and acetate residues varies according to the bacterial strain, the fermentation process, the conditions after fermentation and the purification steps. These groups may be neutralized in commercial products with $Na^+$, $K^+$ or $Ca^{2+}$ ions (Satia company, 1986). The neutralized form may be converted into the acid form by ion exchange or by dialysis of an acidic solution. Xanthan gums have a molecular weight of between 1000000 and 50000000 and a viscosity of between 0.6 Pa·s and 1.65 Pa·s for an aqueous composition containing 1% of xanthan gum (measured at 25° C. on a Brookfield viscometer at 60 rpm). Xanthan gums are represented, for example, by the products sold under the names Rhodicare by the company Rhodia Chimie, under the name Satiaxane™ by the company Cargill Texturizing Solutions (for the food, cosmetic and pharmaceutical industries), under the name Novaxan™ by the company ADM, and under the names Kelzan® and Keltrol® by the company CP-Kelco.

Pullulan is a polysaccharide consisting of maltotriose units, known under the name α(1,4)-α(1,6)-glucan. Three glucose units in maltotriose are connected via an α(1,4) glycoside bond, whereas the consecutive maltotriose units are connected to each other via an α(1,6) glycoside bond. Pullulan is produced, for example, under the reference Pullulan PF 20 by the group Hayashibara in Japan.

Dextran is a neutral polysaccharide not bearing any charged groups, which is biologically inert, prepared by fermentation of beet sugar containing solely hydroxyl groups. It is possible to obtain dextran fractions of different molecular weights from native dextran by hydrolysis and purification. Dextran may in particular be in the form of dextran sulfate. Dextran is represented, for example, by the products sold under the name Dextran or Dextran T by the company Pharmacosmos, or under the name Dextran 40 Powder or Dextran 70 Powder by the company Meito Sangyo Co. Dextran sulfate is sold by the company PK Chemical A/S under the name Dextran sulfate.

Succinoglycan is an extracellular polymer of high molecular weight produced by bacterial fermentation, consisting of octasaccharide repeating units (repetition of 8 sugars). Succinoglycans are sold, for example, under the name Rheozan by the company Rhodia.

Scleroglucan is a nonionic branched homopolysaccharide consisting of β-D-glucan units. The molecules consist of a linear main chain formed from D-glucose units linked via β(1,3) bonds and of which one in three is linked to a side D-glucose unit via a β(1,6) bond. Scleroglucan is sold, for example, under the name Amigel by the company Alban Milner, or under the name Actigum™ CS by the company Cargill.

Gellan gum is an anionic linear heteropolyoside based on oligoside units composed of 4 saccharides (tetraoside). D-Glucose, L-rhamnose and D-glucuronic acid in 2:1:1 proportions are present in gellan gum in the form of monomer elements. It is sold, for example, under the name Kelcogel CG LA by the company CP Kelco.

The polysaccharide according to the invention may be a galactan chosen especially from agar and carrageenans. Carrageenans are anionic polysaccharides constituting the cell walls of various red algae (Rhodophyceae) belonging to the Gigartinacae, Hypneaceae, Furcellariaceae and Polyideaceae families. They are generally obtained by hot aqueous extraction from natural strains of said algae. These linear polymers, formed by disaccharide units, are composed of two D-galactopyranose units linked alternately by α(1,3) and β(1,4) bonds. They are highly sulfated polysaccharides (20% to 50%) and the α-D-galactopyranosyl residues may be in 3,6-anhydro form. Depending on the number and position of sulfate-ester groups on the repeating disaccharide of the molecule, several types of carrageenans are distinguished, namely: kappa-carrageenans, which bear one sulfate-ester group, iota-carrageenans, which bear two sulfate-ester groups and lambda-carrageenans, which bear three sulfate-ester groups. Carrageenans are composed essentially of potassium, sodium, magnesium, triethanolamine and/or calcium salts of polysaccharide sulfate esters. Carrageenans are sold especially by the company SEPPIC under the name Solagum®, by the company Gelymar under the names Carragel®, Carralact® and Carrasol®, by the company Cargill, under the names Satiagel™ and Satiagum™ and by the company CP-Kelco under the names Genulacta®, Genugel® and Genuvisco®.

Galactans of agar type are galactose polysaccharides contained in the cell wall of some of these species of red algae (rhodophyceae). They are formed from a polymer group whose base backbone is a β(1,3) D-galactopyranose and α(1,4) L 3-6 anhydrogalactose chain, these units repeating regularly and alternately. The differences within the agar family are due to the presence or absence of sulfated methyl or carboxyethyl groups. These hybrid structures are generally present in variable percentage, depending on the species of algae and the harvest season.

Agar-agar is a mixture of polysaccharides (agarose and agaropectin) of high molecular mass, between 40000 and 300000 gmol$^{-1}$. It is obtained by manufacturing algal extraction liquors, generally by autoclaving, and by treating these liquors which comprise about 2% of agar-agar, so as to extract the latter.

Agar is produced, for example, by the group B&V Agar Producers under the names Gold Agar, Agarite and Grand Agar by the company Hispanagar and under the names Agar-Agar, QSA (Quick Soluble Agar) and Puragar by the company Setexam.

Furcellaran is obtained commercially from red algae *Furcellaria fasztigiata*. Furcellaran is produced, for example, by the company Est-Agar.

For the purposes of the invention, the term "alginate-based compound" means alginic acid, alginic acid derivatives and salts of alginic acid (alginates) or of said derivatives. Preferably, the alginate-based compound is water-soluble. Alginic acid, a natural substance resulting from brown algae or certain bacteria, is a polyuronic acid composed of 2 uronic acids linked by 1,4-glycosidic bonds: β-D-manuronic acid and α-L-glucuronic acid. Alginic acid is capable of forming water-soluble salts (alginates) with alkali metals such as sodium, potassium or lithium, substituted cations of lower amines and of ammonium such as methylamine, ethanolamine, diethanolamine or triethanolamine. These alginates are water-soluble in aqueous medium at a pH equal to 4, but dissociate into alginic acid at a pH below 4. These alginate-based compounds are capable of crosslinking in the presence of at least one crosslinking agent, by formation of ionic bonds between said alginate-based compounds and said crosslinking agents. The formation of multiple crosslinking between several molecules of said alginate-based compounds leads to the formation of a water-insoluble gel. Use is preferably made of alginate-based compounds with a weight-average molecular mass ranging from 10000 to 1000000, preferably from 15000 to 500000 and better still from 20000 to 250000. According to a preferred embodiment, the alginate-based compound is alginic acid and/or a salt thereof. Advantageously, the alginate-based compound is an alginate salt and preferably sodium alginate. The alginate-based compound may be chemically modified, especially with urea or urethane groups or by hydrolysis, oxidation, esterification, etherification, sulfatation, phosphatation, amination, amidation or alkylation reaction, or by several of these modifications. The derivatives obtained may be anionic, cationic, amphoteric or nonionic. The alginate-based compounds that are suitable for use in the invention may be represented, for example, by the products sold under the names Kelcosol, Satialgine™, Cecalgum™ or Algogel™ by the company Cargill Products, under the name Protanal™ by the company FMC Biopolymer, under the name Grindsted® Alginate by the company Danisco, under the name Kimica Algin by the company Kimica, and under the names Manucol® and Manugel® by the company ISP.

Polysaccharides may be divided into homogeneous polysaccharides (only one saccharide species) and heterogeneous polysaccharides composed of several types of saccharides. Homogeneous polysaccharides according to the invention may be chosen from celluloses and derivatives or fructosans. The polysaccharide according to the invention may also be a cellulose or a derivative thereof, especially cellulose ethers or esters (e.g. methylcellulose, carboxymethylcellulose, hydroxymethylcellulose, hydroxyethylcellulose, hydroxypropylcellulose, hydroxymethylpropylcellulose, cellulose acetate, cellulose nitrate and nitrocellulose). According to the invention, the term "cellulose-based compound" means any polysaccharide compound bearing in its structure linear sequences of anhydroglucopyranose residues (AGU) linked together via β(1,4) bonds. The repeating unit is the cellobiose dimer. The AGUs are in chair conformation and bear 3 hydroxyl functions: 2 secondary alcohols (in position 2 and 3) and a primary alcohol (in position 6). The polymers thus formed combine together via intermolecular bonds of hydrogen bond type, thus giving the cellulose a fibrillar structure (about 1500 molecules per fiber). The degree of polymerization differs enormously depending on the origin of the cellulose; its value may range from a few hundred to several tens of thousands. Among the cellulose derivatives, cellulose ethers, cellulose esters and cellulose ester ethers are distinguished. Among the nonionic cellulose ethers, mention may be made of alkylcelluloses such as methylcelluloses and ethylcelluloses; hydroxyalkylcelluloses such as hydroxymethylcelluloses, hydroxyethylcelluloses and hydroxypropylcelluloses; and mixed hydroxy-alkylalkylcelluloses such as hydroxypropylmethylcelluloses, hydroxyethylmethyl-celluloses, hydroxyethylethylcelluloses and hydroxybutylmethylcelluloses. Among the anionic cellulose ethers, mention may be made of carboxyalkyl celluloses and salts thereof. By way of example, mention may be made of carboxymethylcelluloses, carboxymethylmethylcelluloses and carboxymethylhydroxyethylcelluloses and sodium salts thereof. Among the cationic cellulose ethers, mention may be made of crosslinked or non-crosslinked, quaternized hydroxyethylcelluloses. The quaternizing agent may especially be glycidyltrimethylammonium chloride. Another cationic cellulose ether that may be mentioned is hydroxyethylcellulosehydroxypropyltrimethylammonium. Among the cellulose esters are mineral esters of cellulose (cellulose nitrates, sulfates, phosphates, etc.), organic cellulose esters (cellulose monoacetates, triacetates, amidopropionates, acetatebutyrates, acetatepropionates and acetatetrimellitates, etc.) and mixed organic/mineral esters of cellulose, such as cellulose acetatebutyrate sulfates and cellulose acetatepropionate sulfates. Among the cellulose ester ethers, mention may be made of hydroxypropylmethylcellulose phthalates and ethylcellulose sulfates. The cellulose-based compounds of the invention may be chosen from unsubstituted celluloses and substituted celluloses. The celluloses and derivatives are represented, for example, by the products sold under the names Avicel® (microcrystalline cellulose, MCC) by the company FMC Biopolymers, under the name Cekol (carboxymethylcellulose) by the company Noviant (CP-Kelco), under the name Akucell AF (sodium carboxymethylcellulose) by the company Akzo Nobel, under the name Methocel™ (cellulose ethers) and under the names Aqualon® (carboxymethylcellulose and sodium carboxymethylcellulose), Benecel® (methylcellulose), Blanose™ (carboxymethylcellulose), Culminal® (methylcellulose, hydroxypropylmethylcellulose), Klucel® (hydroxypropylcellulose) and Natrosol® CS (hydroxyethylcellulose) by the company Hercules Aqualon.

The polysaccharide according to the invention may especially be a fructosan chosen from inulin and derivatives thereof (especially dicarboxy- and carboxymethyl-inulins). Fructans or fructosans are oligosaccharides or polysaccharides comprising a sequence of anhydrofructose units optionally combined with several saccharide residues other than fructose. Fructans may be linear or branched. Fructans may be products obtained directly from a plant or microbial source or alternatively products whose chain length has been modified (increased or decreased) by fractionation, synthesis or hydrolysis, in particular enzymatic. Fructans generally have a degree of polymerization from 2 to about 1000 and preferably from 2 to about 60. Three groups of fructans are distinguished. The first group corresponds to products whose fructose units are for the most part linked via $\beta(2,1)$ bonds. These are essentially linear fructans such as inulins. The second group also corresponds to linear fructoses, but the fructose units are essentially linked via $\beta(2,6)$ bonds. These products are levans. The third group corresponds to mixed fructans, i.e. containing $\beta(2,6)$ and $\beta(2,1)$ sequences. These are essentially branched fructans, such as graminans. The fructans used in the compositions according to the invention are inulins. Inulin may be obtained, for example, from chicory, dahlia or Jerusalem artichoke, preferably from chicory. In particular, the polysaccharide, especially the inulin, has a degree of polymerization from 2 to about 1000 and preferably from 2 to about 60, and a degree of substitution of less than 2 on the basis of one fructose unit. The inulin used for this invention is represented, for example, by the products sold under the name Beneo™ inulin by the company Orafti and under the name Frutafit® by the company Sensus.

The polysaccharides that may be used according to the invention may be gums, for instance cassia gum, karaya gum, konj ac gum, gum tragacanth, tara gum, acacia gum or gum arabic. Gum arabic is a highly branched acidic polysaccharide which is in the form of mixtures of potassium, magnesium and calcium salts. The monomer elements of the free acid (arabic acid) are D-galactose, L-arabinose, L-rhamnose and D-glucuronic acid.

Galactomannans (guar, locust bean, fenugreek, tara gum) and derivatives (guar phosphate, hydroxypropyl guar, etc.). Galactomannans are nonionic polyosides extracted from the endosperm of leguminous seeds, of which they constitute the storage carbohydrate. Galactomannans are macromolecules consisting of a main chain of $\beta(1,4)$ linked D-mannopyranose units, bearing side branches consisting of a single D-galactopyranose unit $\alpha(1,6)$ linked to the main chain. The various galactomannans differ, firstly, by the proportion of $\alpha$-D-galactopyranose units present in the polymer and secondly by significant differences in terms of distribution of galactose units along the mannose chain. The mannose/galactose (M/G) ratio is about 2 for guar gum, 3 for tara gum and 4 for locust bean gum.

Guar gum is characterized by a mannose/galactose ratio of the order of 2/1. The galactose group is regularly distributed along the mannose chain. The guar gums that may be used according to the invention may be nonionic, cationic or anionic. According to the invention, use may be made of chemically modified or unmodified nonionic guar gums. The unmodified nonionic guar gums are, for example, the products sold under the names Vidogum GH, Vidogum G and Vidocrem by the company Unipektin and under the name Jaguar by the company Rhodia, under the name Meypro® Guar by the company Danisco, under the name Viscogum™ by the company Cargill and under the name Supercol® guar gum by the company Aqualon. The hydrolyzed nonionic guar gums that may be used according to the invention are represented, for example, by the products sold under the name Meyprodor® by the company Danisco. The modified nonionic guar gums that may be used according to the invention are preferably modified with $C_1$-$C_6$ hydroxyalkyl groups, among which mention may be made, for example, of hydroxymethyl, hydroxyethyl, hydroxypropyl and hydroxybutyl groups. Such nonionic guar gums optionally modified with hydroxyalkyl groups are sold, for example, under the trade names Jaguar HP60, Jaguar HP 105 and Jaguar HP 120 (hydroxypropyl guar) by the company Rhodia or under the name NHance® HP (hydroxypropyl guar) by the company Aqualon. The cationic galactomannan gums preferably have a cationic charge density of less than or equal to 1.5 meq./g, more particularly between 0.1 and 1 meq./g. The charge density may be determined by the Kjeldahl method. It generally corresponds to a pH of the order of 3 to 9. In general, for the purposes of the present invention, the term "cationic galactomannan gum" means any galactomannan gum containing cationic groups and/or groups that can be ionized into cationic groups. The preferred cationic groups are chosen from those comprising primary, secondary, tertiary and/or quaternary amine groups. The cationic galactomannan gums used generally have a weight-average molecular mass of between 500 and $5 \times 10^6$ approximately and preferably between $10^3$ and $1 \times 10^6$ approximately. The cationic galactomannan gums that may be used according to the present invention are, for example, gums comprising tri($C_1$-$C_4$)alkylammonium cationic groups. Preferably, 2% to 30% by number of the hydroxyl functions of these gums bear trialkylammonium cationic groups. Mention may very particularly be made, among these trialkylammonium groups, of the trimethylammonium and triethylammonium groups. Even more preferentially, these groups represent from 5% to 20% by weight relative to the total weight of the modified galactomannan gum. According to the invention, the cationic galactomannan gum is preferably a guar gum comprising hydroxypropyltrimethylammonium groups, i.e. a guar gum modified, for example, with 2,3-epoxypropyltrimethylammonium chloride. Such products are sold especially under the trade names Jaguar EXCEL, Jaguar C13 S, Jaguar C 15, Jaguar C 17 and Jaguar $C_{162}$ (Guar Hydroxypropyltrimonium Chloride) by the company Rhodia, under the name Amilan® Guar (Guar Hydroxypropyltrimonium Chloride) by the company Degussa and under the name N-Hance® 3000 (Guar Hydroxypropyltrimonium Chloride) by the company Aqualon.

The anionic guar gums that may be used according to the invention are polymers comprising groups derived from carboxylic, sulfonic, sulfenic, phosphoric, phosphonic or pyruvic acid. The anionic group is preferably a carboxylic acid group. The anionic group may also be in the form of an acid salt, especially a sodium, calcium, lithium or potassium salt. The anionic guar gums that may be used according to the invention are preferentially carboxymethyl guar derivatives (carboxymethyl guar or carboxymethyl hydroxypropyl guar).

Locust bean gum is extracted from the seeds of the locust bean tree (Ceratonia siliqua). The unmodified locust bean gum that may be used in this invention is sold, for example, under the name Viscogum™ by the company Cargill, under the name Vidogum L by the company Unipektin and under the name Grinsted® LBG by the company Danisco. The chemically modified locust bean gums that may be used in this invention may be represented, for example, by the cationic locust beans sold under the name Catinal CLB (locust bean hydroxypropyltrimonium chloride) by the company Toho.

The tara gum that may be used in the context of this invention is sold, for example, under the name Vidogum SP by the company Unipektin.

Glucomannan is a polysaccharide of high molecular weight ($500000 < M^{glucomannan} < 2000000$) composed of D-mannose and D-glucose units with a branch every 50 or 60 units approximately. It is found in wood, but is also the main constituent of konjac gum. Konjac (*Amorphophallus konjac*) is a plant of the Araceae family. The products that may be used according to the invention are sold, for example, under the names Propol® and Rheolex® by the company Shimizu.

Pectins are linear polymers of α-D-galacturonic acid (at least 65%) linked in positions 1 and 4 with a certain proportion of carboxylic groups esterified with a methanol group. About 20% of the sugars constituting the pectin molecule are neutral sugars (L-rhamnose, D-glucose, D-galactose, L-arabinose, D-xylose). L-Rhamnose residues are found in all pectins, incorporated into the main chain in positions 1,2. Uronic acid molecules bear carboxyl functions. This function gives pectins the capacity for exchanging ions, when they are in COO— form. Divalent ions (in particular calcium) have the capacity of forming ionic bridges between two carboxyl groups of two different pectin molecules.

In the natural state, a certain proportion of the carboxylic groups are esterified with a methanol group. The natural degree of esterification of a pectin may range between 70% (apple, lemon) and 10% (strawberry) depending on the source used. Using pectins with a high degree of esterification it is possible to hydrolyze the —$COOCH_3$ groups, so as to obtain weakly esterified pectins. Depending on the proportion of methylated or non-methylated monomers, the chain is thus more or less acidic. HIM (high-methoxy) pectins are thus defined as having a degree of esterification of greater than 50% and LM (low-methoxy) pectins are defined as having a degree of esterification of less than 50%. In the case of amidated pectins, the —$OCH_3$ group is substituted with an —$NH_2$ group. Pectins are especially sold by the company Cargill under the name Unipectine™, by the company CP-Kelco under the name Genu and by Danisco under the name Grinsted Pectin.

Alternatively, the gelling agent may be synthetic. For the purposes of the invention, the term "synthetic" means that the polymer is neither naturally existing nor a derivative of a polymer of natural origin. The synthetic polymeric gelling agent under consideration according to the invention may or may not be particulate. For the purposes of the invention, the term "particulate" means that the polymer is in the form of particles, preferably spherical particles. As emerges from the text hereinbelow, the polymeric gelling agent is advantageously chosen from crosslinked acrylic homopolymers or copolymers; polyacrylamides and crosslinked and/or neutralized 2-acrylamido-2-methylpropanesulfonic acid polymers and copolymers; modified or unmodified carboxyvinyl polymers and mixtures thereof, especially as defined below.

Particulate synthetic polymeric gelling agents are preferably chosen from crosslinked polymers. They may especially be crosslinked acrylic homopolymers or copolymers, which are preferably partially neutralized or neutralized, and which are in particulate form. According to one embodiment, the particulate gelling agent according to the present invention is chosen from crosslinked sodium polyacrylates. Preferably, it has in the dry or non-hydrated state a mean size of less than or equal to 100 and preferably less than or equal to 50 µm. The mean size of the particles corresponds to the mass-mean diameter measured by laser particle size analysis or another equivalent method known to those skilled in the art. Thus, preferably, the particulate gelling agent according to the present invention is chosen from crosslinked sodium polyacrylates, preferably in the form of particles with a mean size (or mean diameter) of less than or equal to 100 µm, more preferably in the form of spherical particles. As examples of crosslinked sodium polyacrylates, mention may be made of those sold under the brand names Octacare X100, X110 and RM100 by the company Avecia, those sold under the names Flocare GB300 and Flosorb 500 by the company SNF, those sold under the names Luquasorb 1003, Luquasorb 1010, Luquasorb 1280 and Luquasorb 1110 by the company BASF, those sold under the names Water Lock G400 and G430 (INCI name: Acrylamide/Sodium acrylate copolymer) by the company Grain Processing. Mention may also be made of crosslinked polyacrylate microspheres, for instance those sold under the name Aquakeep® 10 SH NF by the company Sumitomo Seika. Such gelling agents may be used in a proportion of from 0.1 wt % to 5 wt % relative to the total weight of the gel phase, especially from 0.5 wt % to 2 wt % and in particular in a proportion of about from 0.8 wt % to 1.7 wt %, relative to the total weight of the gel phase.

Non-particulate synthetic polymeric gelling agents may be detailed under the following subfamilies: 1. Polyacrylamides and crosslinked and/or neutralized 2-acrylamido-2-methylpropane sulfonic acid polymers and copolymers, and 2. Modified or unmodified carboxyvinyl polymers.

With respect to polyacrylamides and crosslinked and/or neutralized 2-acrylamido-2-methylpropanesulfonic acid polymers and copolymers, the polymers used that are suitable as aqueous gelling agent for the invention may be crosslinked or non-crosslinked homopolymers or copolymers comprising at least the 2-acrylamidomethylpropanesulfonic acid (AMPS®) monomer, in a form partially or totally neutralized with a mineral base such as sodium hydroxide or potassium hydroxide. They are preferably totally or almost totally neutralized, i.e. at least 90% neutralized. These AMPS® polymers according to the invention may be crosslinked or non-crosslinked. When the polymers are crosslinked, the crosslinking agents may be chosen from the polyolefinically unsaturated compounds commonly used for crosslinking polymers obtained by radical polymerization. Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylene-diamine, tetraallyloxyethane, trimethylolpropane diallyl ether, allyl (meth)acrylate, allylic ethers of alcohols of the sugar series, or other allylic or vinyl ethers of polyfunctional alcohols and also the allylic esters of phosphoric and/or vinylphosphonic acid derivatives, or mixtures of these compounds. According to one preferred embodiment of the invention, the crosslinking agent is chosen from methylenebisacrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer. The AMPS® polymers that are suitable for use in the invention are water-soluble or water-dispersible. In this case, they are: (1) either "homopolymers" comprising only AMPS monomers and, if they are crosslinked, one or more crosslinking agents such as those defined above; or (2) copolymers obtained from AMPS® and from one or more hydrophilic or hydrophobic ethylenically unsaturated monomers and, if they are crosslinked, one or more crosslinking agents such as those defined above. When said copolymers comprise hydrophobic ethylenically unsaturated monomers, these monomers do not comprise a fatty chain and are preferably present in small amounts. For the purpose of the present invention, the term "fatty chain" means any hydrocarbon-based chain comprising at least 7 carbon atoms. The term "water-soluble or water-dispersible" means polymers which, when introduced into an aqueous phase at 25° C., at a mass concentration equal to 1%, make it possible to obtain a macroscopically homogeneous and transparent solution, i.e. a solution with a maximum light transmittance value, at a wavelength equal to 500 nm, through a sample 1 cm thick, of at least 60% and preferably of at least 70%. The water-soluble or water-dispersible AMPS® copolymers according to the invention contain water-soluble ethylenically unsaturated monomers, hydrophobic monomers, or mixtures thereof. The water-soluble comonomers may be ionic or nonionic. Among the ionic water-soluble comonomers, examples that may be mentioned include the following compounds and salts thereof: (meth)acrylic acid, styrenesulfonic acid, vinylsulfonic acid and (meth)allylsulfonic acid, vinylphosphonic acid, maleic acid, itaconic acid and crotonic acid. Among the nonionic water-soluble comonomers, examples that may be mentioned include: (meth) acrylamide, N-vinylacetamide and N-methyl-N-vinylacetamide, N-vinylformamide and N-methyl-N-vinylformamide, maleic anhydride, vinylamine, N-vinyllactams comprising a cyclic alkyl group containing from 4 to 9 carbon atoms, such as N-vinylpyrrolidone, N-butyrolactam and N-vinylcaprolactam and vinyl alcohol of formula $CH_2=CHOH$. Mention is made, for example, of glycidyl (meth)acrylate, hydroxyethyl methacrylate, and (meth)acrylates of ethylene glycol, of diethylene glycol or of polyalkylene glycol. Among the hydrophobic comonomers without a fatty chain, mention may be made, for example, of styrene and derivatives thereof, such as 4-butylstyrene, α-methylstyrene and vinyltoluene; vinyl acetate of formula $CH_2=CH-OCOCH_3$; vinyl ethers of formula $CH_2=CHOR$ in which R is a linear or branched, saturated or unsaturated hydrocarbon-based radical containing from 1 to 6 carbon atoms; acrylonitrile; caprolactone; vinyl chloride and vinylidene chloride; and silicone derivatives, which, after polymerization, result in silicone polymers such as methacryloxypropyltris(trimethylsiloxy)silane and silicone methacrylamides. Mention is made, for example, of methyl methacrylate, ethyl methacrylate, n-butyl (meth)acrylate, tert-butyl (meth)acrylate, cyclohexyl acrylate, isobornyl acrylate and 2-ethylhexyl acrylate. The water-soluble or water-dispersible AMPS® polymers of the invention preferably have a molar mass ranging from 50000 g/mol to 10000000 g/mol, preferably from 80000 g/mol to 8000000 g/mol and even more preferably from 100000 g/mol to 7000000 g/mol. As water-soluble or water-dispersible AMPS homopolymers suitable for use in the invention, mention may be made, for example, of crosslinked or non-crosslinked polymers of sodium acrylamido-2-methylpropanesulfonate, such as that used in the commercial product Simulgel 800 (CTFA name: Sodium Polyacryloyldimethyl Taurate), crosslinked ammonium acrylamido-2-methylpropanesulfonate polymers (INCI name: Ammonium Polydimethyltauramide) such as those described in patent EP0815928 and such as the product sold under the trade name Hostacerin AMPS® by the company Clariant. As preferred water-soluble or water-dispersible AMPS homopolymers in accordance with the invention, mention may be made of crosslinked ammonium acrylamido-2-methylpropanesulfonate polymers. As water-soluble or water-dispersible AMPS copolymers in accordance with the invention, examples that may be mentioned include: (a) crosslinked acrylamide/sodium acrylamido-2-methylpropanesulfonate copolymers, such as that used in the commercial product Sepigel 305 (CTFA name: Polyacrylamide/$C_{13}$-$C_{14}$ Isoparaffin/Laureth-7) or that used in the commercial product sold under the name Simulgel 600 (CTFA name: Acrylamide/Sodium acryloyldimethyltaurate/Isohexadecane/Polysorbate-80) by the company SEPPIC; (b) copolymers of AMPS® and of vinylpyrrolidone or vinylformamide, such as that used in the commercial product sold under the name Aristoflex AVC® by the company Clariant (CTFA name: Ammonium Acryloyldimethyltaurate/VP copolymer) but neutralized with sodium hydroxide or potassium hydroxide; (c) copolymers of AMPS® and of sodium acrylate, for instance the AMPS/sodium acrylate copolymer, such as that used in the commercial product sold under the name Simulgel EG® by the company SEPPIC; and (d) copolymers of AMPS® and of hydroxyethyl acrylate, for instance the AMPS®/hydroxyethyl acrylate copolymer, such as that used in the commercial product sold under the name Simulgel NS® by the company SEPPIC (CTFA name: Hydroxyethyl acrylate/sodium acryloyldimethyltaurate copolymer (and) squalane (and) polysorbate 60), or such as the product sold under the name Sodium acrylamido-2-methylpropanesulfonate/hydroxyethyl acrylate copolymer, such as the commercial product Sepinov EM or Sepinov EMT 10 (INCI name: Hydroxyethyl acrylate/Sodium acryloyldimethyltaurate copolymer). As preferred water-soluble or water-dispersible AMPS copolymers in accordance with the invention, mention may be made of copolymers of AMPS® and of hydroxyethyl acrylate. In general, a gel phase according to the invention may comprise from 0.1 wt % to 12 wt %, preferably from 0.3 wt % to 10 wt % and more preferentially from 0.5 wt % to 8 wt % of polyacrylamide(s) and/or of crosslinked and/or neutralized 2-acrylamido-2-methylpropanesulfonic acid polymer(s) and copolymer(s) relative to its total weight.

The modified or unmodified carboxyvinyl polymers may be copolymers derived from the polymerization of at least one monomer (a) chosen from α,β-ethylenically unsaturated carboxylic acids or esters thereof, with at least one ethylenically unsaturated monomer (b) comprising a hydrophobic group. The term "copolymers" means both copolymers obtained from two types of monomer and those obtained from more than two types of monomer, such as terpolymers obtained from three types of monomer. In particular, among the modified or unmodified carboxyvinyl polymers, mention may also be made of sodium polyacrylates such as those sold under the name Cosmedia SP® containing 90% solids and 10% water, or Cosmedia SPL® as an inverse emulsion containing about 60% solids, an oil (hydrogenated polydecene) and a surfactant (PPG-5 Laureth-5), both sold by the company Cognis. Mention may also be made of partially neutralized sodium polyacrylates that are in the form of an inverse emulsion comprising at least one polar oil, for example the product sold under the name Luvigel® EM sold by the company BASF. The modified or unmodified carboxyvinyl polymers may also be chosen from crosslinked (meth)acrylic acid homopolymers. For the purposes of the present invention, the term "(meth)acrylic" means "acrylic or methacrylic". Examples that may be mentioned include the products sold by Lubrizol under the names Carbopol 910, 934, 940, 941, 934 P, 980, 981, 2984, 5984 and Carbopol Ultrez 10 and 30 Polymer, or by 3V-Sigma under the name Synthalen® K, Synthalen® L or Synthalen® M. Preferably the gelling agent is Carbopol Ultrez, more specifically Carbopol Ultrez 30 polymer. Among the modified or unmodified carboxyvinyl polymers, mention may be made in particular of Carbopol (CTFA name: carbomer) and Pemulen (CTFA name: Acrylates/$C_{10}$-$C_{30}$ alkyl acrylate crosspolymer) sold by the company Lubrizol. The modified or unmodified carboxyvinyl polymers may be present in a proportion of from 0.1 wt % to 10 wt % relative to the weight of the gel phase, in particular from 0.3 wt % to 8 wt % and preferably between 0.4 wt % and 6 wt % relative to the weight of the gel phase.

Advantageously, a composition according to the invention comprises at least one synthetic polymeric gelling agent, preferably chosen from crosslinked and/or neutralized 2-acrylamido-2-methylpropanesulfonic acid polymers and copolymers and modified or unmodified carboxyvinyl polymers. According to a preferred variant, the synthetic polymeric hydrophilic gelling agent is chosen from crosslinked ammonium acrylamido-2-methylpropanesulfonate polymers, copolymers of AMPS® and of hydroxyethyl acrylate and crosslinked (meth)acrylic acid homopolymers, preferably copolymers of AMPS® and of hydroxyethyl acrylate.

Alternatively, the gelling agents are chosen from mixed silicates and fumed silicas. For the purposes of the present invention, the term "mixed silicate" means all silicates of natural or synthetic origin containing several (two or more) types of cations chosen from alkali metals (for example $Na^+$, $Li^+$, $K^+$) or alkaline-earth metals (for example $Be^{2+}$, $Mg^{2+}$, $Ca^{2+}$) transition metals and aluminum. According to a particular embodiment, the mixed silicate(s) are in the form of solid particles containing at least 10 wt % of at least one silicate relative to the total weight of the particles. In the rest of the present description, these particles are referred to as "silicate particles". Preferably, the silicate particles contain less than 1 wt % of aluminum relative to the total weight of the particles. In particular, it is an alkali metal or alkaline-earth metal, aluminum or iron silicate or mixture of silicates. Preferably, it is sodium, magnesium and/or lithium silicate. To ensure good cosmetic properties, these silicates are generally in a finely divided form, and in particular in the form of particles with a mean size ranging from 2 nm to 1 μm (from 2 nm to 1000 nm), preferably from 5 nm to 600 nm and even more preferentially from 20 to 250 nm. The silicate particles may have any form, for example the form of spheres, flakes, needles, platelets, disks, leaflets, or totally random forms. Preferably, the silicate particles are in the form of disks or leaflets. Thus, the term "mean size" of the particles means the numerical mean size of the largest dimension (length) that it is possible to measure between two diametrically opposite points on an individual particle. The size may be determined, for example, by transmission electron microscopy or by measuring the specific surface area via the BET method or by laser particle size analysis. When the particles are in the form of disks or leaflets, they generally have a thickness ranging from about 0.5 nm to 5 nm. The silicate particles may consist of an alloy with metal or metalloid oxides, obtained, for example, by thermal melting of the various constituents thereof. When the particles also comprise such a metal or metalloid oxide, this oxide is preferably chosen from silicon, boron or aluminum oxide. According to a particular embodiment of the invention, the silicates are phyllosilicates, namely silicates having a structure in which the $SiO_4$ tetrahedra are organized in leaflets between which the metal cations are enclosed. The mixed silicates that are suitable for use in the invention may be chosen, for example, from montmorillonites, hectorites, bentonites, beidellite and saponites. According to a preferred embodiment of the invention, the mixed silicates used are more particularly chosen from hectorites and bentonites and better still from laponites. A family of silicates that is particularly preferred in the compositions of the present invention is thus the laponite family. Laponites are sodium magnesium silicates also possibly containing lithium, which have a layer structure similar to that of montmorillonites. Laponite is the synthetic form of the natural mineral known as hectorite. The synthetic origin of this family of silicates is of considerable advantage over the natural form, since it allows good control the composition of the product. In addition, laponites have the advantage of having a particle size that is much smaller than that of the natural minerals hectorite and bentonite. Laponites that may especially be mentioned include the products sold under the following names: Laponite® XLS, Laponite® XLG, Laponite® RD, Laponite® RDS, Laponite® XL21 (these products are sodium magnesium silicates and sodium lithium magnesium silicates) by the company Rockwood Additives Limited. Such gelling agents may be used in a proportion of from 0.1 wt % to 8 wt % relative to the total weight of the gel phase, especially from 0.1 wt % to 5 wt % and in particular from 0.5 wt % to 3 wt %, relative to the total weight of the gel phase.

The fumed silicas according to the present invention are hydrophilic. The hydrophilic fumed silicas are obtained by pyrolysis of silicon tetrachloride ($SiCl_4$) in a continuous flame at 1000° C. in the presence of hydrogen and oxygen. Among the fumed silicas of hydrophilic nature that may be used according to the present invention, mention may especially be made of those sold by the company Degussa or Evonik Degussa under the trade names Aerosil® 90, 130, 150, 200, 300 and 380 or alternatively by the company Cabot under the name Carbosil H5. Such gelling agents may be used in a proportion of from 0.1 wt % to 10 wt % relative to the total weight of the gel phase, especially from 0.1 wt % to 5 wt % and in particular from 0.5 wt % to 3 wt % relative to the total weight of the gel phase.

In one embodiment, the gel phase has a pH of between 2 and 9, preferably between 3 and 8, more preferably between 3.5 and 7.5.

Additional Components that May be in the Gel Phase and/or Cream Phase

The compositions of the present invention may comprise additional components. The additional components may be found in the cream phase, the gel phase, other phases if included, and/or all of these phases. The concentration of the components stated below relate to the concentrations within the specific phases unless otherwise stated.

Colourant

In one particular embodiment, at least one of the phases comprises a colourant so that the phases are visually distinct from one another. These colourants may also bring a colour and an aesthetic effect to the skin to which it is applied. In one embodiment the colourant is added to the gel phase.

In one embodiment, the colourant is contained in one or more phases at a level by weight of between 0.00005% and 10%, preferably between 0.0001% and 7%, more preferably between 0.0002% and 5%. In one embodiment, among the colourants, pigments are contained in one or more phases at a level by weight of between 0.001% and 0.5%, preferably between 0.005% and 0.2%, more preferably between 0.005% and 0.1%. These concentration ranges are specific to the phase that the colourant and/or pigment is within, rather than the total composition.

The colourant may be in the form of a particle. The particles useful herein are water-insoluble, and preferably have a particle size of between 5 nm and 5 µm, more preferably between 5 nm and 2 µm, still more preferably between 5 nm and 1 µm. The particles useful herein are preferably those having a density of 0.8 g/cm$^3$ or higher, more preferably 0.9 g/cm$^3$ or higher.

By colourant, it is necessary to include white or colored, mineral or organic particles (nacre type), insoluble in an aqueous solution, intended to color and/or to opacify the resulting film. Mention may be made, as inorganic pigments which can be used in the invention, of titanium, zirconium or cerium oxides, as well as oxides of zinc, iron or chromium, ferric blue, manganese violet, ultramarine blue and chromium hydrate.

According to one particular embodiment, the colourant comprises at least coated iron oxides and/or coated titanium oxides, preferably coated with aluminum stearoyl glutamate or perfluoroalkyl phosphate.

According to another particular embodiment, the colourant comprises titanium oxides, preferably titanium dioxide sold under the name Flamenco Summit Gold Y30D by BASF Personal Care Ingredients (INCI name: Mica (and) titanium dioxide) and/or titanium dioxide coated with perfluoroalkyl phosphate, in particular sold under the name PF 5 TiO$_2$ A 100 by Daito Kasei Kogyo (INCI name: titanium dioxide (and) C$_9$ to C$_{15}$ fluoroalcohol phosphate) and coated or uncoated iron oxides.

The term "nacres" is understood to mean colored particles of any shape, iridescent or otherwise, in particular produced by certain shells in their shells or else synthesized and which exhibit an effect of color by optical interference.

Examples of nacres include nacreous pigments such as titanium mica coated with an iron oxide, mica coated with bismuth oxychloride, titanium mica coated with chromium oxide, nacreous pigments based on bismuth oxychloride. They may also be mica particles on the surface of which are superimposed at least two successive layers of metallic oxides and/or organic coloring matter.

According to a particular embodiment, the dyestuffs are inorganic colourants chosen from titanium oxides, iron oxides and mixtures thereof.

Minerals, such as talc or mica, as well as boron nitride, may be used as colourants in the context of the present invention. Synthetic equivalents to these minerals can also be used. For example fluorphlogopite, a synthetic material very similar to mica, may be used.

Polymers can be used to form colourants of the present invention. Polymers may be silicone or non-silicone based. Non-silicone based polymers include nylon, polyamides such as polyhexamethylene adipamide (PA66), polycaproamide (PA6), PA6.10, PA10.10 and PA12, polyesters, polyolefins, polymers based on a cellulose ester, such as cellulose acetate, cellulose propionate, rayon, viscose and polymers of the same family, acrylic polymers, such as poly(methyl methacrylate) and copolymers, copolymers in any proportions of these polymers and blends between any of these polymers. Preferably the polymer is nylon, such as nylon 6/12, nylon 66, nylon 6, nylon 510 or nylon 1,6 (preferably nylon 6/12). Silica (or a combination of a polymer of silica) may also be used to form the colourant.

Examples of Sensient polymer include COVABEAD LH 85 (methyl methacrylate cross polymer with a matte effect), COVABEAD LH 170 (methyl methacrylate cross polymer with a creamy feeling), COVABEAD PMMA (polymethyl methacrylate with a powdery feeling), COVABEAD VELVET 10 (polymethyl methacrylate with a superior softness effect), COVABEAD VELVET 20 (polymethyl methacrylate with a superior ball-bearing effect) and COVABEAD PMMA 2 MUSI (polymethyl methacrylate with silica).

Suitable Shin Etsu silicone-based polymer include KMP-590 (polymethylsilsesquioxane at an average diameter of 2 µm), KMP-591 (polymethylsilsesquioxane at an average diameter of 5 µm), KSP-100 (vinyl dimethicone/methicone silsesquioxane crosspolymer at an average diameter of 5 µm), KSP-101 (vinyl dimethicone/methicone silsesquioxane crosspolymer at an average diameter of 12 µm), KSP-102 (vinyl dimethicone/methicone silsesquioxane crosspolymer at an average diameter of 30 µm), KSP-105 (vinyl dimethicone/methicone silsesquioxane crosspolymer at an average diameter of 2 µm), KSP-300 (diphenyl dimethicone/vinyl diphenyl dimethicone/silsesquioxane crosspolymer), KSP-411 (polysilicone-1 crosspolymer) and KSP-441 (polysilicone-22).

Borosilicates can be used to form colourant. Suitable borosilicate platelets include violet interference pearl. Suitable borosilicate particles include HOLLOW CORE SILICATE R3178 from Sensient, a calcium aluminium borosilicate.

Glass can be used to form colourant. Suitable glass particles include COVABEAD CRYSTAL from Sensient, which are transparent spherical beads.

According to a particular embodiment, the colourant particles are coated. Preferably this coating is with triethoxycaprylylsilane.

Anti-Inflammatory Agent

In one embodiment, the composition comprises at least one anti-inflammatory agent. The term "anti-inflammatory agent" is intended to mean an agent which provides an anti-inflammatory benefit as would be understood by a person skilled in the art.

The anti-inflammatory agent may be selected from the group consisting of a glycyrrhizic acid or glycyrrhizic acid derivative (such as monoammonium glycyrrhizate (MAG)), panthenol, α-bisabolol, betaine, lipochroman, tocopheryl acetate, phytosphingosine, extracts of green tea, extracts of *Sophora flavescens*, extracts of chamomile (e.g. *Anthemis nobilis*), extracts of *Aloe vera*, extracts of *Echinacea*, extracts of willow bark, extracts of willow herb, extracts of almond, extracts of oats, extracts of *Kola*, extracts of red clover, salicylic acid, xymeninic acid, turmeric, urea, hydroxyureas, glycerol, polyglycerols, AQUAXYL™, glycerolglucoside and combinations thereof.

The anti-inflammatory agent may be present in an amount that produces an inhibitory effect on interleukin-6 (IL-6). For example, the anti-inflammatory agent may produce more than about 40% interleukin-6 inhibition, more than about 50% interleukin-6 inhibition, more than about 60% interleukin-6 inhibition, more than about 70% interleukin-6 inhibition, more than about 75% interleukin-6 inhibition, more than about 80% interleukin-6 inhibition, more than about 90% interleukin-6 inhibition, more than about 99% interleukin-6 inhibition, or 100% interleukin-6 inhibition. A suitable technique for measuring IL-6 inhibition is readily known in the art.

The anti-inflammatory agent may be present in one or more phases in an amount of about 0.0001 wt % to about 20 wt %, about 0.001 wt % to about 15 wt %, about 0.01 wt % to about 10 wt %, about 0.1 wt % to about 5 wt % or about 1 wt % to about 3 wt %. In one embodiment, the anti-inflammatory agent is present in one or more phases in an amount of about 1.5 wt % to about 3 wt %. These concentration ranges are specific to the phase that the anti-inflammatory agent is within, rather than the total composition.

Anti Oxidant

The antioxidant may be a polyphenolic agent. The antioxidant may comprise extracts from plants chosen from Raspberry, Oregano (e.g. *Origanum vulgare*), Green tea (for example green leaves of *Camellia sinensis*), White tea (for example *Camellia sinensis*), Blueberry extract (for example *Vaccinium cyanococcus*), French maritime pine bark (for example *Pinus pinaster*, sold under the trade name Pycnogenol), Rosemary (for example *Rosmarinus officialis*), Grape, including grape seed (for example *Vitis vinifera*), Fennel (for example *Foeniculi fructus*), *Caragana sinica*, Marjoram (for example *Origanum majorana*), Crocus (for example *Crocus sativus*), Apple (for example *Malus domestica*), Mulberry (for example *Morus alba*), Ginseng (for example *Panax ginseng*), Coffee, Green coffee, Cherry (for example *Prunus avium*), Snow algae (for example *Chlamydomonas nivalis*), Emblica (for example *Phyllanthus emblica*), Gingko (for example *Gingko biloba*), Moringa (for example *Moringa oleilera*), Ginger (for example *Zingiberaceae*), Magnolia (for example *Magnolioideae virginiana*), French saffron, Edelweiss (for example *Leontopodium alpinium*), White lotus (for example *Nymphaea alba*), Turmeric root, Marshmallow (for example *Althaea officianlis*), Burdock (for example *Arctium lappa*), Bilberry (for example *Vaccinium myrtillus*), Cranberry (for example *Vaccinium oxycoccus*), Pomegranate nectar (for example *Punica granatum*), Sage (for example *Salvia officinalis*), Thyme (for example *Thymus vulgaris*), Sunflower (for example *Helianthus annuus*), wild carrot (for example *Daucus carota*), Hop (for example *Humulus lupulus*), Witch Hazel (for example *Hamamelis*), Oak (for example *Quercus*), Camellia (for example *Theacea*), Red clover (for example *Tritolium pratense*), Flax (for example *Linium usitatissimum*), lemon (for example *Citrus limon*), birch (for example *Betula*), cornflower, (for example *Centaurea cyanus*), geranium, polygonum, soy (for example *Glycine max*) and mixtures thereof.

In one embodiment the antioxidant polyphenolic agent may be an extract from a plant chosen from mulberry, ginseng, grape, oregano, grape, sage, sunflower, maritime pine bark, rosemary, marjoram, *crocus*, French saffron, wild carrot, hop, coffee, green coffee, witch hazel, oak, *camellia*, red clover, flax, ginger, magnolia, edelweiss, burdock and mixtures thereof.

Active polyphenolic species sourced from the above list of plants include those chosen from apigenin, luteolin, quercetin, kaempferol, naringenin, hesperetin, catechin, gallocatechin, cyaniding, pelargonidin, daidzein, caffeic acid, chlorogenic acid, romsmarinic acid, gallic acid, resveratrol, ferulic acid, epigallocatechin gallate, piceatannol, secoisolariciresinol, isotaxiresinol, Miyabenol c, Luteolin and mixtures thereof.

The anti-oxidant may be a vitamin and derivatives thereof, in particular the esters thereof, such as retinol (vitamin A) and the esters thereof (retinyl palmitate for example), ascorbic acid (vitamin C) and the esters thereof, ascorbic acid sugar derivatives (such as for example ascorbyl glucoside), tocopherol (vitamin E) and the esters thereof (such as for example tocopherol acetate) and vitamin $B_3$ or $B_{10}$ (niacinamide and derivatives thereof).

The amounts of antioxidant agents used in the present invention are expressed as dry weights of the extract or of the concentrated vitamin, as understood by a man skilled in the art. In one embodiment one or more phases comprise one or more antioxidants at a concentration of between 0 wt % or about 0.005 wt % and about 10 wt %. Preferably the antioxidant is present in one or more phases at a concentration of between about 0.01 wt % and about 7 wt %. More preferably the antioxidant is present in one or more phases at a concentration of between about 0.01 wt % and about 5 wt %. These concentration ranges are specific to the phase that the antioxidant agent is within, rather than the total composition.

Skin Conditioning Agent

The composition of the present invention may optionally comprise a skin conditioning agent. The skin conditioning agents may be chosen from humectants, emollients, moisturisers, or mixtures thereof.

The skin conditioning agents may be chosen from guanidine, urea, glycolic acid, glycolate salts, salicylic acid, lactic acid, lactate salts, *Aloe vera*, polyhydroxy alcohols (such as sorbitol, mannitol, xylitol, erythritol, glycerol, hexanetriol, butanitriol, (di) propylene glycol, butylene glycol, hexylene glycol, polyethylene glycol), sugars (for example fructose, glucose, xylose, honey, mannose, xylose), gluconodeltalactone, starches and derivatives thereof, pyrrolidone, lactamide monoethanolamine, acetamide monoethanolamine, panthenol, allantoin, glycerine, ethylhexyl glycerine, arabinoglactan, PPG-15 stearyl ether, ethylhexyl stearate, cetyl dimethicone, octyldodecanol, PPG-20 methyl glucose ether, isopropyl myristate, isopropyl palmitate, isopropyl laurate, isodecyl laurate, isodecyl neopentanoate, isohexadecane, pentaerythrityl tetraisostearate, caprylic/capric triglyceride, canola oil, sunflower oil (*Helianthus annus*), olive oil (*Olea europea*), cottonseed oil (*Gossypium herbaceum*), jojoba oil (*Simmondsia chinensis*), shea butter (*Butyrospermum parkii*), cocoa butter (*Theobroma cacao*), cupuacu butter (*Theobroma grandiflorum*), avocado oil (*Peryea gratissima*), liquid paraffin, dimethicone, phenyl trimethicone, cyclopentasiloxane, dimethiconol, bisaccharide gum, isononyl isononoate, carnauba wax and/or petrolatum.

In one embodiment, the composition comprises hyaluronic acid and/or a salt thereof. Hyaluronic acid protects collagen levels, keeping skin supple, as well as maintaining skin moisture. Preferably the hyaluronic acid and/or salt thereof would be present in the gel phase. By "salts thereof", it is meant that, as well as hyaluronic acid, hyaluronate, and any of its hyaluronate salts, are also covered here. In one embodiment, the salts of hyaluronate and sodium, potassium, lithium, magnesium, calcium, or combinations thereof (preferably sodium). The molecular mass of hyaluronic acid/hyaluronate is not particularly limited and may be, for example, between $1.0 \times 10^3$ Da and $1.0 \times 10^7$ Da, preferably between $5.0 \times 10^3$ Da and $5.0 \times 10^6$ Da.

In one embodiment, one or more phases comprise one or more skin conditioning agents (including hyaluronic acid and/or a salt thereof) at a concentration of between 0 wt % or 0.01 wt % and 20 wt %. Preferably the skin conditioning agent is present in one or more phases at a concentration of between 0.1 wt % and 10 wt %. More preferably the skin conditioning agent is present in one or more phases at a concentration of between 0.5 wt % and 7 wt %. These concentration ranges are specific to the phase that the skin conditioning agent is within, rather than the total composition.

Preservatives

Preservatives may be added to the composition such as phenoxyethanol, benzoic acid, sodium benzoate, sorbic acid, potassium sorbate, 2-bromo2-nitropropane-1,3-diol (bronopol, which is available commercially under the trade name Myacide®), benzyl alcohol, benzoic acid, sodium benzoate, diazolidinyl urea, imidazolidinyl urea, methyl paraben, ethyl paraben, propyl paraben, sodium methyl paraben, sodium dehydroacetate, dehydroacetic acid, polyhexamethylenebiguanide hydrochloride, isothiazolone, chlorhexidine digluconate, chlorphensin and/or sodium propyl paraben. In one embodiment, the preservative is added to both the cream phase and the gel phase. In one embodiment, the preservative is phenoxyethanol. In one embodiment, the cosmetic composition of the invention does not comprise parabens.

In one embodiment one or more phases comprise one or more preservatives at a concentration of between 0.001 wt % and about 5 wt %. Preferably one or more phases comprise one or more preservatives at a concentration of between about 0.01 wt % and about 4 wt %. More preferably one or more phases comprise one or more preservatives at a concentration of between about 0.1 wt % and about 2.5 wt %. These concentration ranges are specific to the phase that the preservative is within, rather than the total composition.

Sequestering Agents or Chelating Agents.

Sequestering agents and/or chelating agents may be added to the composition, such as ethylenediamine tetraacetic acid (EDTA) and salts thereof (for example dipotassium EDTA, disodium EDTA or tetrasodium EDTA), sodium phytate, trisodium ethylene diamine disuccinate and/or tetrasodium glutamate diacetate.

In one embodiment one or more phases comprise one or more sequestering agents or chelating agents at a concentration of between about 0.001 wt % and about 10 wt %. Preferably one or more phases comprise one or more sequestering agents or chelating agents at a concentration of between about 0.01 wt % and about 8 wt %. More preferably one or more phases comprise one or more sequestering agents or chelating agents at a concentration of between about 0.02 wt % and about 5 wt %. These concentration ranges are specific to the phase that the sequestering agent and/or chelating agent is within, rather than the total composition.

Waxes

The composition may include a wax. By "wax" it is meant an organic compound that is a hydrophobic, malleable solid at and near ambient temperatures. Examples include higher alkanes (i.e. hydrocarbon compounds of the formula $C_nH_{2n+2}$, where n is at least 18, more commonly at least 20 or at least 24, and n is typically up to 40, or up to 60) lipids, including mono-, di- and tri-glycerides and phospholipids, and long-chain fatty acids. Waxes typically have melting points above about 40° C. Waxes are insoluble in water (by which is meant having a solubility in distilled water of less than about 1 gram per 100 mL, and typically less than 0.5 gram or less than 0.1 gram per 100 mL), but are generally soluble in organic, nonpolar solvents.

Preferably the wax is a long-chain mono- or di-glyceride or a mixture of such compounds.

By long-chain mono- or di-glycerides is meant glycerides with one or two fatty acid residues, those fatty acid residues being are greater than 12 carbon atoms in length and preferably greater than 16 carbon atoms.

Most preferably the long-chain mono- or diglyceride contains fatty acid residues of length greater than 20 carbon atoms. Most preferably the mono- or diglyceride is glyceryl behenate. In particularly preferred embodiments, the behenate is a combination of mono- and dibehenate as found in glyceryl behenate EP/NF supplied under the trade name Compritol 888 ATO.

Other suitable waxes may include plant and animal waxes such as carnauba wax and beeswax, petrolatum waxes such as microcrystalline wax, and long chain aliphatic esters such as cetyl palmitate. Further examples include long-chain (typically C12 and above) fatty acids that are solid at ambient temperature, such as palmitic acid, behenic acid and stearic acid, as well as esters of dicarboxylic acids such as fumaric, succinic and sebacic acid (e.g. dibutyl sebacate, diethyl sebacate and alkyl fumarates and alkyl succinates). Certain polyethylene glycols (PEGs) that are solid at ambient temperature may also be suitable, e.g. PEG6000 and analogues thereof).

In one embodiment one or more phases comprise one or more waxes at a concentration of between 0 wt % or 0.01 wt % and about 10 wt %. This concentration range is specific to the phase that the wax is within, rather than the total composition.

pH Adjusting Agents

The composition may also include pH adjusting agents such as potassium hydroxide, sodium hydroxide, amino methyl propanol sodium citrate and/or triethanolamine. The composition may be buffered by means well known in the art, for example by use of buffer systems comprising succinic acid, citric acid, lactic acid and acceptable salts thereof, phosphoric acid, mono- or disodium phosphate and sodium carbonate.

In one embodiment, one or more phases comprise one or more pH adjusting agents at a concentration of between 0.01 wt % and 10 wt %. This concentration range is specific to the phase that the pH adjusting agent is within, rather than the total composition.

Thickener, Viscosity Modifying Agent or Gelling Agent

A thickener and/or viscosity modifying agent may be added to the composition. Preferably the thickener and/or viscosity modifying agent is polymeric. Examples of such polymeric thickeners or viscosity modifying agents include acrylic acid polymers, for example available commercially under the trade name Ultrez® or Carbopol® (both Lubrizol) (preferably Ultrez®), taurate copolymers such as acryloyl methyl taurate-vinylpyrrolidone copolymers, alkylated polyvinylpyrrolidone copolymers (such as Anatron™ V220), hydroxyethylacrylate/sodium acryloyldimethyl taurate copolymers, modified celluloses, for example hydroxyethylcelluloses available commercially under the trade name Natrosol® (Hercules), hydroxypropylmethyl celluloses, block polymers of ethylene oxide and propylene oxide (for example, those available from BASF Wyandotte under the trade name "Pluronic"®), decadiene crosspolymers (available under the trade name Stabilez® 60), Aristoflex® AVC (Clariant), xanthan gums, starches, or modified starches (such as a metal salt of starches, for example aluminium salts of the reaction product of 1-octenylsuccinic anhydride with starches), sodium polyacrylates, polyvinyl alcohols and alkyl galactmanans available under the trade name N-Hance® from Hercules.

Alternatively the thickener and/or viscosity modifying agent may be non-polymeric. Examples of such non-polymeric thickener, viscosity modifying agent and gelling agents include amine oxides, ethoxylated fatty alcohols, salts (such magnesium chloride, sodium chloride) phthalic acid amides and fatty alcohols. In addition, the non-polymeric thickener may be inorganic. Inorganic thickeners include silica and clay materials such as bentonite, hectorite and montmorillonite. Specific examples of clay materials include disteardimonium hectorite and stearalkonium hectorite (these materials form part of the Bentone® gel range from Elementis). These inorganic thickeners may be hydrophobically modified. Examples of silica that have been hydrophobically modified are silica silylate and silica dimethyl silylate (available as part of the Aerosil® range from Evonik).

Bitter Substance

As there is potential for this skincare composition to be confused with a striped toothpaste, it is preferable for the composition to comprise a bitter substance in order to reduce the amount ingested if it were confused with a toothpaste. Suitable bitter substances are preferably aromatic oils, preferably peppermint oil, *eucalyptus* oil, bitter almond oil, menthol, fruit aroma substances, preferably aroma substances from lemons, oranges, limes, grapefruit, denatonium compounds or mixtures thereof. Denatonium compounds are particularly preferred. Denatonium compounds are commonly available in the form of denatonium benzoate (Bitrex®) or denatonium saccharide. Preferably the bitter substance is present in both the gel phase and the cream phase.

In one embodiment, one or more phases comprise a bitter substance at a concentration of between 0.01 wt % and 2 wt % relative to the cream phase or the gel phase, preferably between 0.05 wt % and 1 wt %, more preferably between 0.08 wt % and 1.0 wt %. These concentration ranges are specific to the phase that the bitter substance is within, rather than the total composition.

Active Agents

Among the active ingredients that can be associated with the composition that is the subject matter of this invention, mention may be made for example of: compounds showing a slimming or lipolytic action such as caffeine or derivatives thereof, ADIPOSLIM™, ADIPOLESS™; N-acylated proteins; N-acylated peptides such as for example MATRIXIL™; N-acylated amino acids; partial hydrolysates of N-acylated proteins; amino acids; peptides; total protein hydrolysates, soya bean extracts, for example Raffermine™; wheat extracts, for example TENSINE™ or GLIADINE™; fresh or sea water alga extracts; marine extracts in general such as corals; bacterial extracts; ceramides; phospholipids; compounds showing an antimicrobial action or a purifying action, such as for example LIPACIDE™ CBG, LIPACIDE™ UG, SEPICONTROL™ A5; OCTOPIROX™ or SENSIVA™ SC50; the compounds showing an energising or tonic property such as Physiogenyl™, panthenol and derivatives thereof such as SEPICAP™ MP; anti-aging agents such as SEPILIFT™ DPHP, SEPIVINOL™, SEPIVITAL™, MANOLIVA™, PHYTO-AGE™, TIMECODE™; SURVICODE™, LIPACIDE™ PVB; anti-photoaging agents; agents protecting the integrity of the dermoepidermic junction; agents increasing the synthesis of components of the extracellular matrix such as for example collagen, elastins, glycosaminoglycans; agents promoting chemical cell communication such a cytokines or physical cell communication such as integrins; agents creating a "warming" sensation on the skin such as skin microcirculation activators (such as for example nicotinic acid derivatives); or products creating a "cooling" sensation on the skin (such as for example menthol and derivatives); agents improving skin microcirculation, for example veinotonics; draining agents; agents for decongestant purposes such as for example extracts of *Gingko biloba*, ivy, horse chestnut, bamboo, ruscus, butcher's broom, *Centalla asiatica*, fucus, rosemary and willow.

Of course, those skilled in the art will be careful to select any complementary compounds and/or their quantity in such a way that the advantageous properties intrinsically attached to the composition present in the container of the present invention and its packaging and distribution with the device according to the invention do not are not, or substantially not, altered by the proposed addition.

Viscosity of the Gel and Cream Phases in Relation to One Another

The invention relates specifically to how to stabilise cream and gel phases of a multi-phase composition with respect to one phase moving without the other phase when the viscosity of the cream phase differs from the viscosity of the gel phase. As such, the viscosity ratio of the cream phase to the gel phase in the multi-phase composition of the present invention is 1.25 or greater:1 or 1.1.25 or greater. In one embodiment, the viscosity ratio of the cream phase to the gel phase is 1.3 or greater:1 or 1.1.3 or greater. In a further embodiment, the viscosity ratio of the cream phase to the gel phase is 1.35 or greater:1 or 1.1.35 or greater. In a further embodiment, the viscosity ratio of the cream phase to the gel phase is 1.4 or greater:1 or 1.1.4 or greater.

Alternatively viewed, the viscosity of the cream phase is higher than the viscosity of the gel phase by 25% or greater or the viscosity of the gel phase is higher than the viscosity of the cream phase by 25% or greater. In one embodiment, the viscosity of the cream phase is higher than the viscosity of the gel phase by 30% or greater or the viscosity of the gel phase is higher than the viscosity of the cream phase by 30% or greater. In a further embodiment, the viscosity of the cream phase is higher than the viscosity of the gel phase by 35% or greater or the viscosity of the gel phase is higher than the viscosity of the cream phase by 35% or greater. In a further embodiment, the viscosity of the cream phase is higher than the viscosity of the gel phase by 40% or greater or the viscosity of the gel phase is higher than the viscosity of the cream phase by 40% or greater.

Alternatively viewed, in one embodiment the viscosity of the cream phase and the gel phase vary by more than 10 Pa·s. In a preferred embodiment, the viscosity of the cream phase and the gel phase vary by more than 12 Pa·s.

This invention is particularly suited to situations where the viscosity of the cream phase cannot be decreased in order to match the viscosity of the gel phase and the viscosity of the gel phase cannot be increased in order to match the viscosity of the cream phase. As such, in one embodiment the viscosity of the cream phase is greater than the viscosity of the gel phase. More specifically, in one embodiment the viscosity ratio of the cream phase to the gel phase in the multi-phase composition of the present invention is 1.25 or greater:1. In one embodiment, the viscosity ratio of the cream phase to the gel phase is 1.3 or greater:1. In a further embodiment, the viscosity ratio of the cream phase to the gel phase is 1.35 or greater:1. In a further embodiment, the viscosity ratio of the cream phase to the gel phase is 1.4 or greater:1. Alternatively viewed, the viscosity of the cream phase is higher than the viscosity of the gel phase by 25% or greater or the viscosity of the gel phase is higher than the viscosity of the cream phase by 25% or greater. In one embodiment, the viscosity of the cream phase is higher than the viscosity of the gel phase by 30% or greater. In a further embodiment, the viscosity of the cream phase is higher than the viscosity of the gel phase by 35% or greater. In a further embodiment, the viscosity of the cream phase is higher than the viscosity of the gel phase by 40%.

In one embodiment, the viscosity ratio of the cream phase to the gel phase is from 1:3 to 3:1. In a further embodiment, the viscosity ratio of the cream phase to the gel phase is from 1:2.9 to 2.9:1. In a further embodiment, the viscosity ratio of the cream phase to the gel phase is from 1:2.8 to 2.8:1. In a further embodiment, the viscosity ratio of the cream phase to the gel phase is from 1:2.7 to 2.7:1. In a further embodiment, the viscosity ratio of the cream phase to the gel phase is from 1:2.6 to 2.6:1. In a further embodiment, the viscosity ratio of the cream phase to the gel phase is from 1:2.5 to 2.5:1. In a further embodiment, the viscosity ratio of the cream phase to the gel phase is from 1:2.4 to 2.4:1. In a further embodiment, the viscosity ratio of the cream phase to the gel phase is from 1:2.3 to 2.3:1. In a further embodiment, the viscosity ratio of the cream phase to the gel phase is from 1:2.2 to 2.2:1.

Ratio of Cream Phase to Gel Phase

The inventors have surprisingly found that the ratio of the cream phase to the gel phase within the multi-phase composition is critical for maintaining the stability of a multi-phase composition with respect to one phase moving without the other phase. In particular, a similar amount of cream phase and gel phase are necessary in order for the multi-phase composition to be stable. The cream phase and the gel phase within the multi-phase composition of the present invention are present in the composition at a level such that the weight ratio of the cream phase to the gel phase is within the range of from 65:35 to 35:65. In one embodiment the cream phase and the gel phase within the multi-phase composition of the present invention are present in the composition at a level such that the weight ratio of the cream phase to the gel phase is within the range of from 60:40 to 40:60. In a further embodiment the cream phase and the gel phase within the multi-phase composition of the present invention are present in the composition at a level such that the weight ratio of the cream phase to the gel phase is within the range of from 58:42 to 42:58. In a further embodiment the cream phase and the gel phase within the multi-phase composition of the present invention are present in the composition at a level such that the weight ratio of the cream phase to the gel phase is within the range of from 56:44 to 44:56. In a further embodiment the cream phase and the gel phase within the multi-phase composition of the present invention are present in the composition at a level such that the weight ratio of the cream phase to the gel phase is within the range of from 54:46 to 46:54. In a further embodiment the cream phase and the gel phase within the multi-phase composition of the present invention are present in the composition at a level such that the weight ratio of the cream phase to the gel phase is within the range of from 52:48 to 48:52.

Packaging

The multi-phase composition of the present invention is preferably packaged within a collapsible tube in a similar manner to, for example, a toothpaste. However, in an alternative embodiment, the multi-phase composition may be packaged within a pot or jar. The advantage of a tube packaging is that a consistent ratio of the cream phase and the gel phase can be extruded from the outlet bore, whilst with a pot or a jar the ratio of the cream phase and of the gel phase is likely to vary each time a consumer extracts some of the composition therefrom.

When a tube is used as packaging, it has an elongated squeezable and deformable body, which is open at its bottom end until the tube is filled. Thereafter it is crimped, heat sealed, sonic welded or otherwise closed at its bottom. The tube is provided with a neck which optionally has external threading adapted to receive a cap thereon for closing. The neck is provided with an outlet bore through which the multi-phase composition contained in the tube may be extruded through. Preferably interconnecting the neck with the body is a tapered conical shoulder portion.

In one aspect, the present invention provides a collapsible tube having an outlet bore and containing the multi-phase composition as described above, wherein the tube is filled such that, when the composition is extruded from the outlet bore, the extruded composition comprises the cream phase and the gel phase that are visually distinct from one another and within a weight ratio of the cream phase to the gel phase of between 65:35 and 35:65 across the cross-section of the extrusion. By "cross-section" it is meant that, when viewing into the tube through the centre of the outlet bore when the multiphase composition is being extruded out, the composition as seen from that angle would comprise the cream phase and the gel phase that are visually distinct from one another and within a weight ratio of the cream phase to the gel phase of between 65:35 and 35:65. In one embodiment, the tube is filled such that, when the composition is extruded from the outlet bore, the extruded composition comprises the cream phase and the gel phase that are visually distinct from one another and within a weight ratio of the cream phase to the gel phase of between 60:40 and 40:60 across the cross-section of the extrusion. In a further embodiment, the tube is filled such that, when the composition is extruded from the outlet bore, the extruded composition comprises the cream phase and the gel phase that are visually distinct from one another and within a weight ratio of the cream phase to the gel phase of between 58:42 and 42:58 across the cross-section of the extrusion. In a further embodiment, the tube is filled such that, when the composition is extruded from the outlet bore, the extruded composition comprises the cream phase and the gel phase that are visually distinct from one another and within a weight ratio of the cream phase to the gel phase of between 56:44 and 44:56 across the cross-section of the extrusion. In a further embodiment, the tube is filled such that, when the composition is extruded from the outlet bore, the extruded composition comprises the cream phase and the gel phase that are visually distinct from one another and within a weight ratio of the cream phase to the gel phase of between 54:46 and 46:54 across the cross-section of the extrusion. In a further embodiment, the tube is filled such that, when the composition is extruded from the outlet bore, the extruded composition comprises the cream phase and the gel phase that are visually distinct from one another and within a weight ratio of the cream phase to the gel phase of between 52:48 and 48:52 across the cross-section of the extrusion.

In one embodiment, the collapsible tube is filled such that, when the composition is extruded from the outlet, the composition forms a visually distinct pattern selected from the following list: striped, marbled, check, mottled, veined, speckled, ribbons, helical, grooved, ridged, waved, sinusoidal, spiral, contoured, weave or woven, such as basket weave and combinations thereof. In a preferred embodiment, the collapsible tube is filled such that, when the composition is extruded from the outlet, the composition forms a striped pattern.

Use of the Composition

The multi-phase composition of the present invention may be used on skin (preferably human skin) for the purpose of any one of moisturizing skin (including hydrating skin), improving the radiance of the skin, improving skin suppleness, reducing skin tightness, nourishing skin and/or reducing dryness, or any combination thereof. Preferably the multi-phase composition is used to moisturize/hydrate skin. The multi-phase composition may be used on any part of the skin, but preferably the composition is used on any one or more of the face (including lips), neck skin and/or décollete (more preferably the face).

Method of Manufacture

The composition of the present invention may be prepared by any known or otherwise effective technique, suitable for making and formulating the desired multi-phase product form. It is especially effective to use toothpaste-tube filling technology for this purpose, especially when the packaging is a collapsible tube.

The skilled person will understand that optional features of one embodiment or aspect of the invention may be applicable, where appropriate, to other embodiments or aspects of the invention.

There now follows by way of example only a description of the present invention with reference to the accompanying drawings, in which.

Figure 1A:
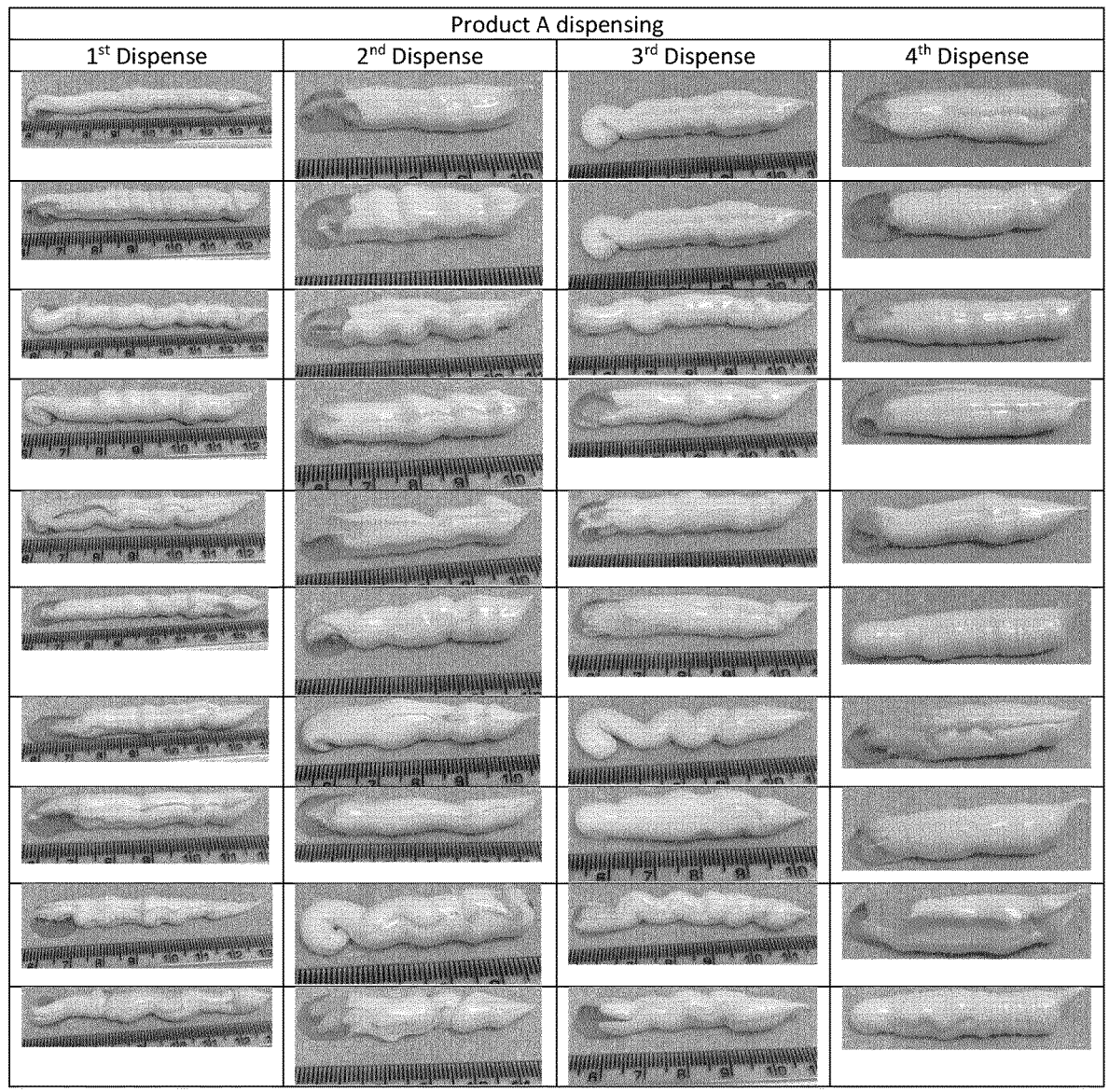
FIG. 1 shows portions of a composition consisting of 80% cream phase as presented in Table 1 and 20% gel phase as presented in Table 2 (Product A) after it is dispensed from a collapsible tube. Fourteen portions of the composition were dispensed from ten tubes at a rate of one portion per day.

FIG. 4 shows portions of the composition consisting of 80% cream phase as presented in Table 1 and 20% gel phase as presented in Table 2 (Product A), consisting of 50% cream phase as presented in Table 1 and 50% gel phase as presented in Table 2 (Product B) and consisting of 20% cream phase as presented in Table 1 and 80% gel phase as presented in Table 2 (Product C) after the compositions were subject to transit testing for a period of half an hour, two hours or eight hours within a collapsible tube and then dispensed therefrom.

EXAMPLES

Example 1—Manufacture of Two Phases of the Paste

A cream phase and a gel phase were created comprising constituents as presented in Tables 1 and 2 below:

TABLE 1

| Cream Phase | |
| --- | --- |
| Material Name | Concentration (% w/w) |
| White soft paraffin BP | 3.00 |
| $C_{12}$-$C_{15}$ alcohols benzoate | 5.75 |
| Abil WE09 (by Evonik, containing | 3.00 |

TABLE 1-continued

| Cream Phase | |
| --- | --- |
| Material Name | Concentration (% w/w) |
| 34% polyglyceryl-4 isostearate, 33% cetyl PEG/PPG-10/1 dimethicone and 33% hexyl laurate) | |
| Abil EM90 (by Evonik, cetyl PEG/PPG-10/1 dimethicone) | 1.00 |
| Sequestrene tetrasodium | 0.05 |
| Isononyl isononanoate | 2.75 |
| Humectant | 5.00 |
| Magnesium sulphate BP super pearl | 0.90 |
| Preservative | 0.80 |
| Bitrex Solution MACFS (Denatonium benzoate) | 0.10 |
| Purified water BP | q.s. 100 |

TABLE 2

| Gel Phase | |
| --- | --- |
| Material Name | Concentration (% w/w) |
| Humectant | 10.00 |
| Carbopol Ultrez 30 polymer (by Lubrizol, carbomer) | 1.00 |
| Blue No1 FD&C | 0.0003 |
| Keltrol RD (by CP Kelco, xanthan gum) | 0.80 |
| Hyaluronic acid (35%) and sodium hyaluronate (65%) | 1.00 |
| Sequestrene $Na_4$ | 0.05 |
| Preservative | 0.40 |
| pH adjuster | 0.90 |
| Bitrex Solution MACFS (Denatonium benzoate) | 0.10 |
| Purified water BP | q.s. 100 |

The cream phase was manufactured using the following method: In a main vessel the oil phase ingredients ($C_{12}$-$C_{15}$ alcohols benzoate, white soft paraffin BP, Abil WE09, Abil EM90 and isononyl isononanoate) were combined through stirring at 55° C. to 60° C. In a support vessel the aqueous phase ingredients (water, sequestrene tetrasodium, magnesium sulphate BP super pearl, preservative, bitrex solution MACFS and humectant) were combined through stirring for one to two minutes between additions at 55° C. to 60° C. The contents of the support vessel was then slowly combined with the main vessel contents with high-speed stirring, ensuring that no water-pooling takes place. The main vessel contents is then cooled to 25° C. before homogenization at 3500 rpm for 1 minute. Finally, 5 minutes of stirring was carried out.

The gel phase was manufactured using the following method: 1% of the water was added to the blue No1 FD&C colourant in a support vessel. The rest of the water was added to the main vessel. Sequestrene tetrasodium and humectant were added whilst stirring. Hyaluronic acid was then added whilst stirring at a high speed, followed by homogenization for 1 to 2 minutes at 3500 rpm. The Carbopol Ultrez polymer was then added whilst stirring at a high speed, followed by homogenization for 1 to 2 minutes at 3500 rpm. The Keltrol RD was then added through homogenization for 3 to 5 minutes at 3500 rpm. Preservative was then added whilst stirring. Bitrex solution MACFS was then added whilst stirring. The blue No1 FD&C colourant solution was then added whilst stirring. The pH adjuster was then added whilst stirring.

Example 2—Viscosity Determination

The viscosity of the gel and cream phases was determined. Viscosity as described in the present application is measured using a Brookfield RVDV-I Prime viscometer plus Model G Laboratory Stand, equipped with a heliopath and either the TBar Spindle C (otherwise known as spindle 93) for the cream phase or the TBar Spindle B (otherwise known as spindle 92) for the gel phase. Viscosity measurements were obtained as follows: (1) Ensure the sample product has a temperature of 23° C. and that it is not aerated. Sample is presented in a 120 ml capacity plastic container; (2) Before measurement, auto-zero the viscometer after switching on the unit by following the on-screen instructions with no spindle attached to the viscometer; (3) Select either TBar Spindle C (with respect to the cream phase) or TBar Spindle B (with respect to the gel phase); (4) Select the revolution speed "10". This will rotate the spindle at 10 revolutions per minute (rpm); (5) Carefully attach the spindle to the lower shaft of the viscometer; (6) Press the "Timed Option" buttons; (7) Use the Up and Down arrows to select the "Timed Stop" option then press "Enter" to confirm; (8) Use the Up and Down arrows to select zero minutes, then press "Enter" to confirm; (9) Use the Up and Down arrows to select 30 seconds, then press "Enter" to confirm; (10) Press the "Motor On/Off" button to begin the measurement; (11) The viscometer will display a countdown from 30 seconds, after which it will display the final viscosity measured; and (12) Record the viscosity.

The gel phase had a viscosity of between 23 Pa·s and 31 Pa·s. The cream phase had a viscosity of between 45 Pa·s and 55 Pa·s. It is also noted that, for both the gel phase and the cream phase, a similar initial torque reading was measured, confirming that the TBar Spindle C used for the cream phase is comparable to the TBar Spindle B used for the gel phase.

Example 3—Filling of the Cream and Gel Phases into a Tube

The cream and gel phases were placed into a divided nozzle which keeps the cream phase and gel phase separate. An even and consistent pressure was then applied to the nozzle in order to dispense the nozzle content into a tube in the form of a stripe (one stripe of the cream phase and one stripe of the gel phase). The tubes were filled so that the contained one of (i) 80% cream and 20% gel (Product A); (ii) 50% cream and 50% gel (Product B); and 20% cream and 80% gel (Product C).

Example 4—Dispense Testing

This study was carried out in order to determine whether an even distribution of the gel and cream phases is obtained when a portion of the combined product is dispensed from the tube each day. The size of the portion dispensed was designed to mimic the amount that a consumer would dispense in order to achieve the desired application requirements (in this particular instance for application on the entire face).

Each day, at approximately the same time of the day, for fourteen days approximately 4 ml of the combined product was dispensed by hand so as to form a stripe on a solid, flat surface and a picture was taken. This was carried out with respect to ten tubes for each product.

Figure 1B:
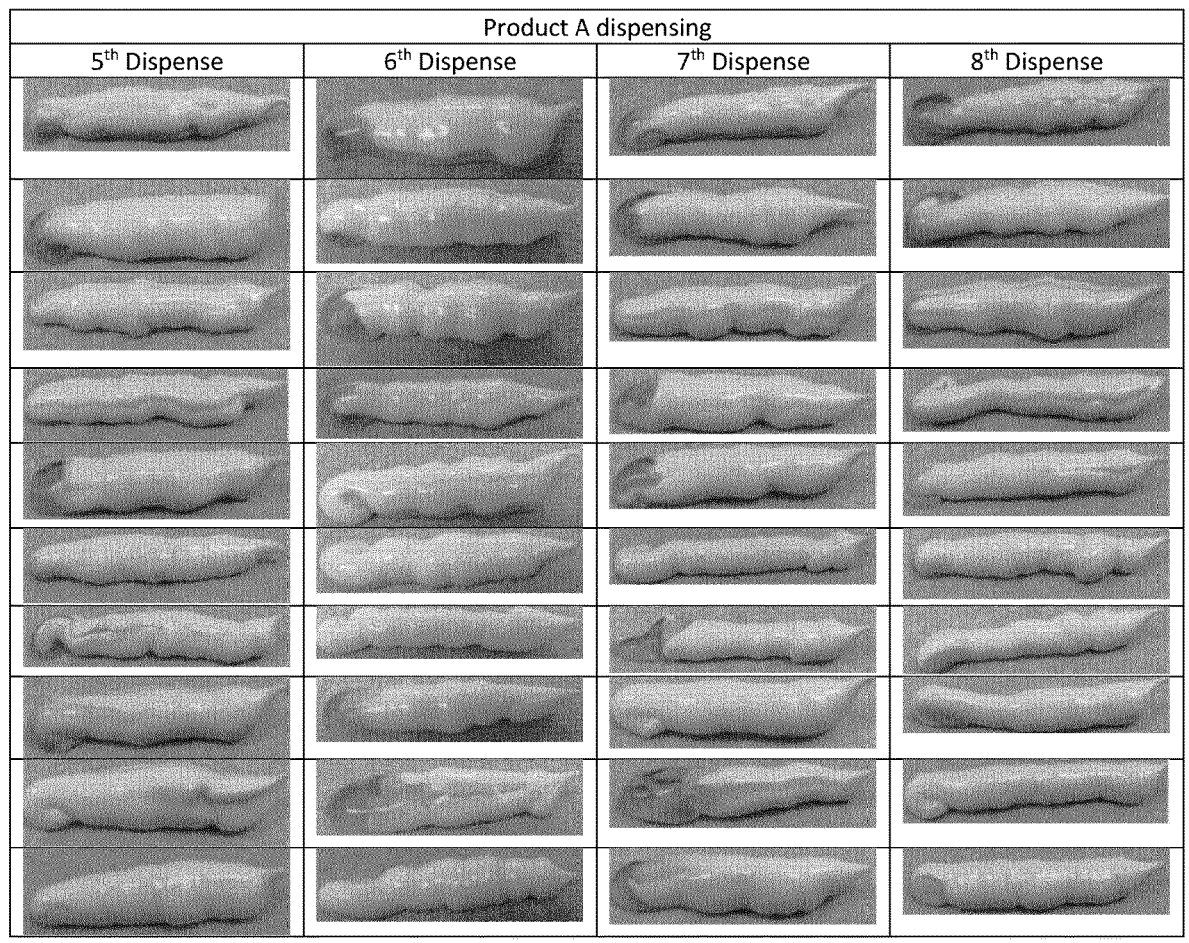
Figure 1C:
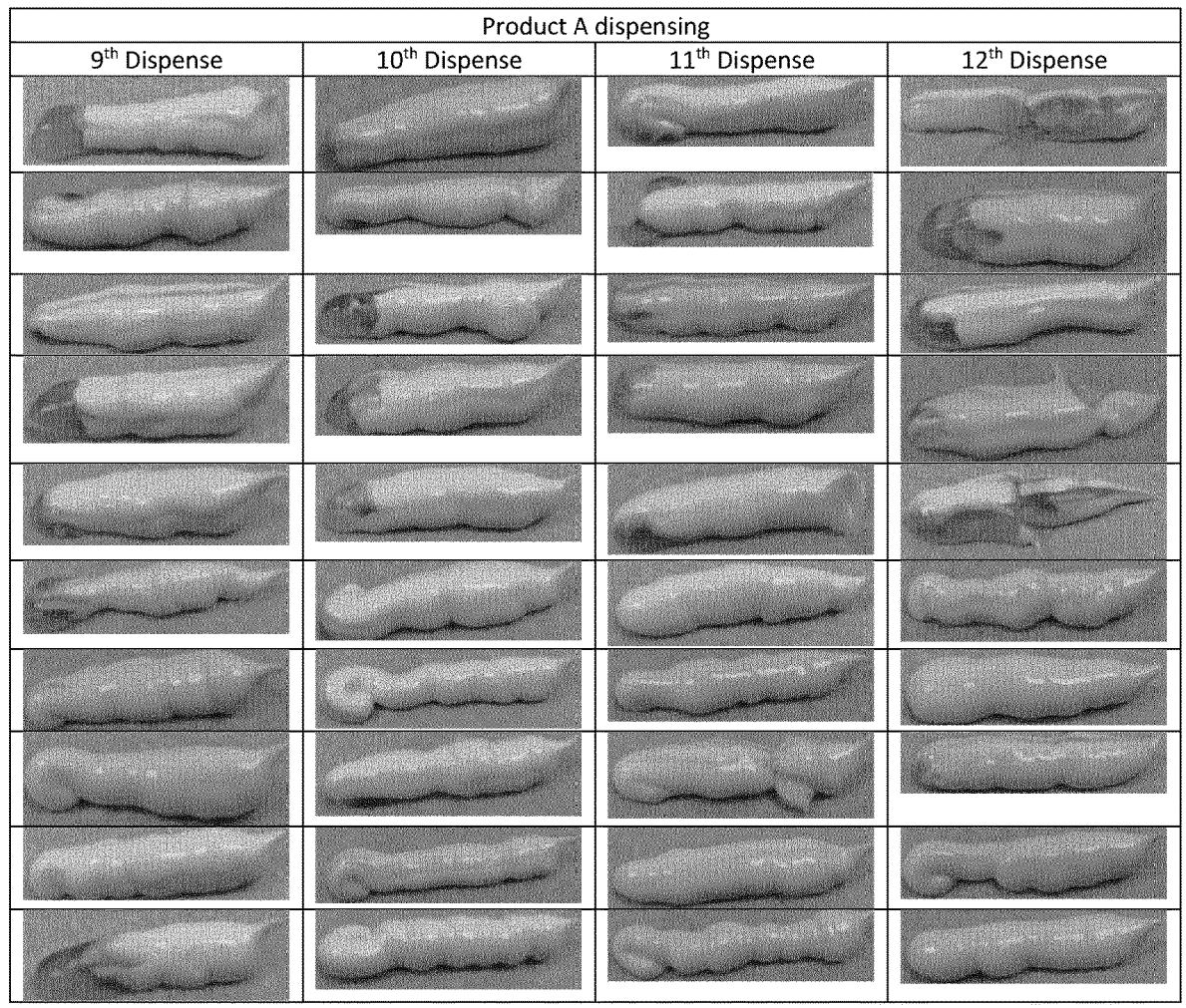
Figure 1D:
Figure 2A:
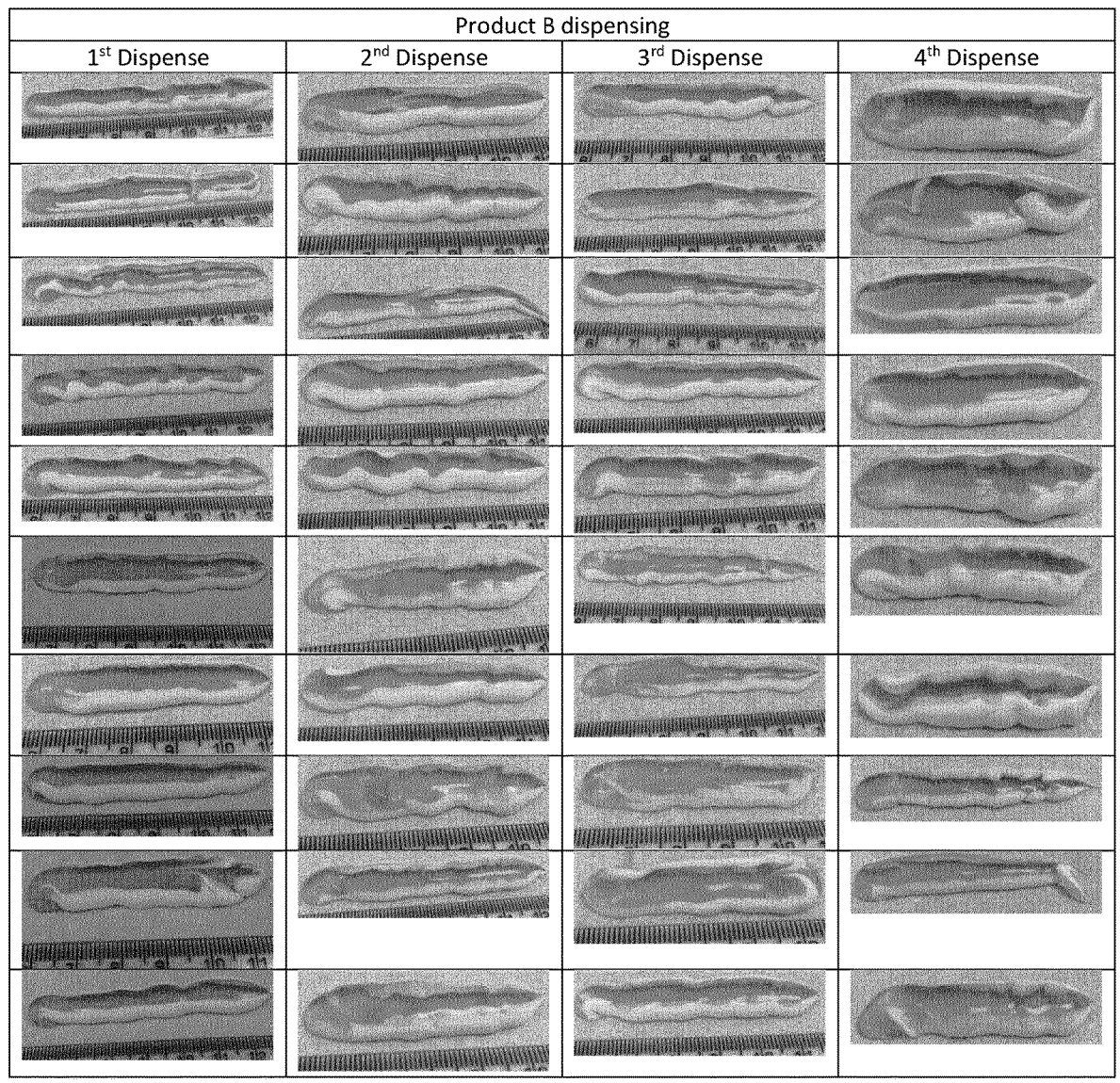
FIG. 2 shows portions of a composition consisting of 50% cream phase as presented in Table 1 and 50% gel phase as presented in Table 2 (Product B) after it is dispensed from a collapsible tube. Fourteen portions of the composition were dispensed from ten tubes at a rate of one portion per day.
Figure 2B:
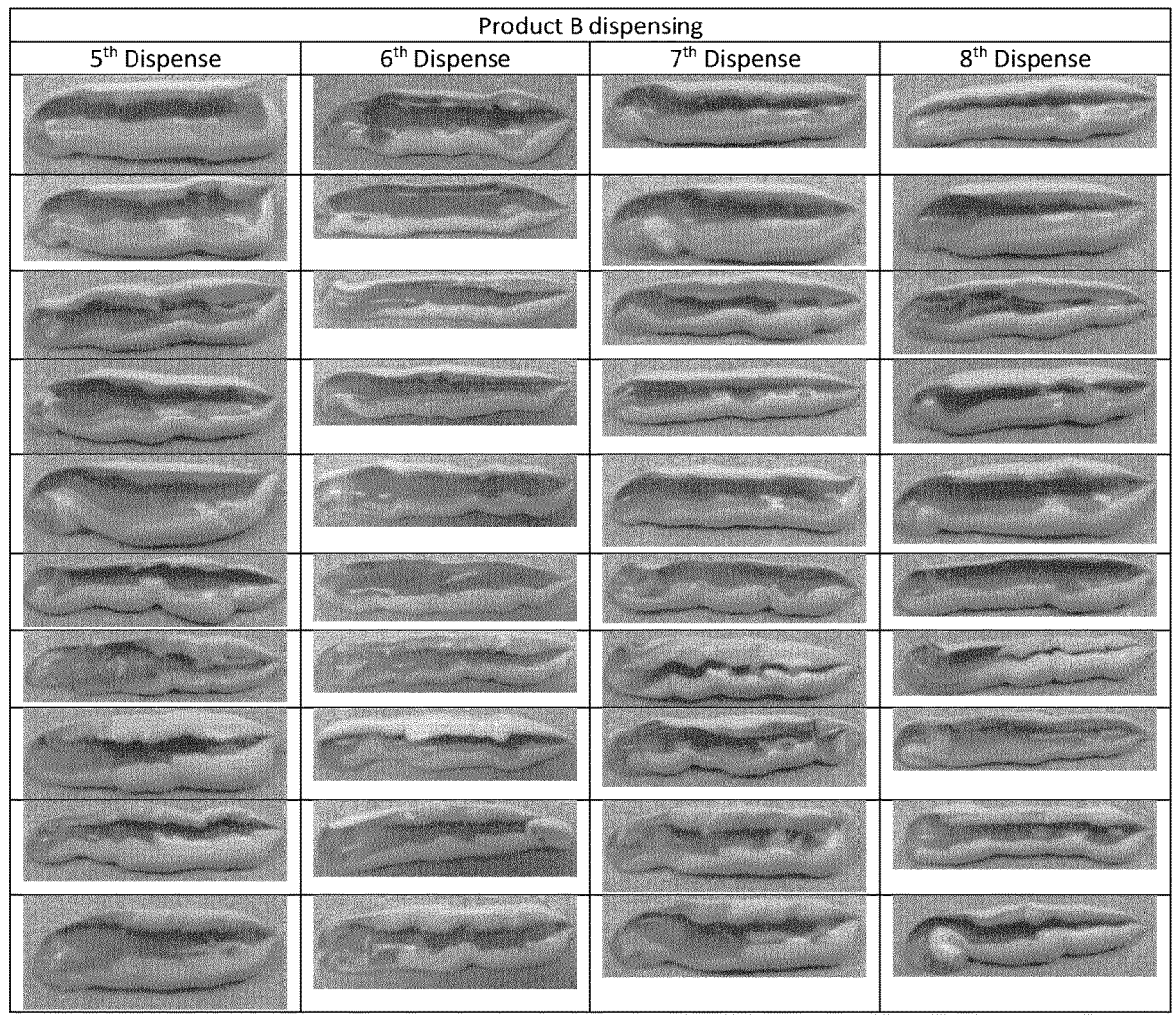
Figure 2C:
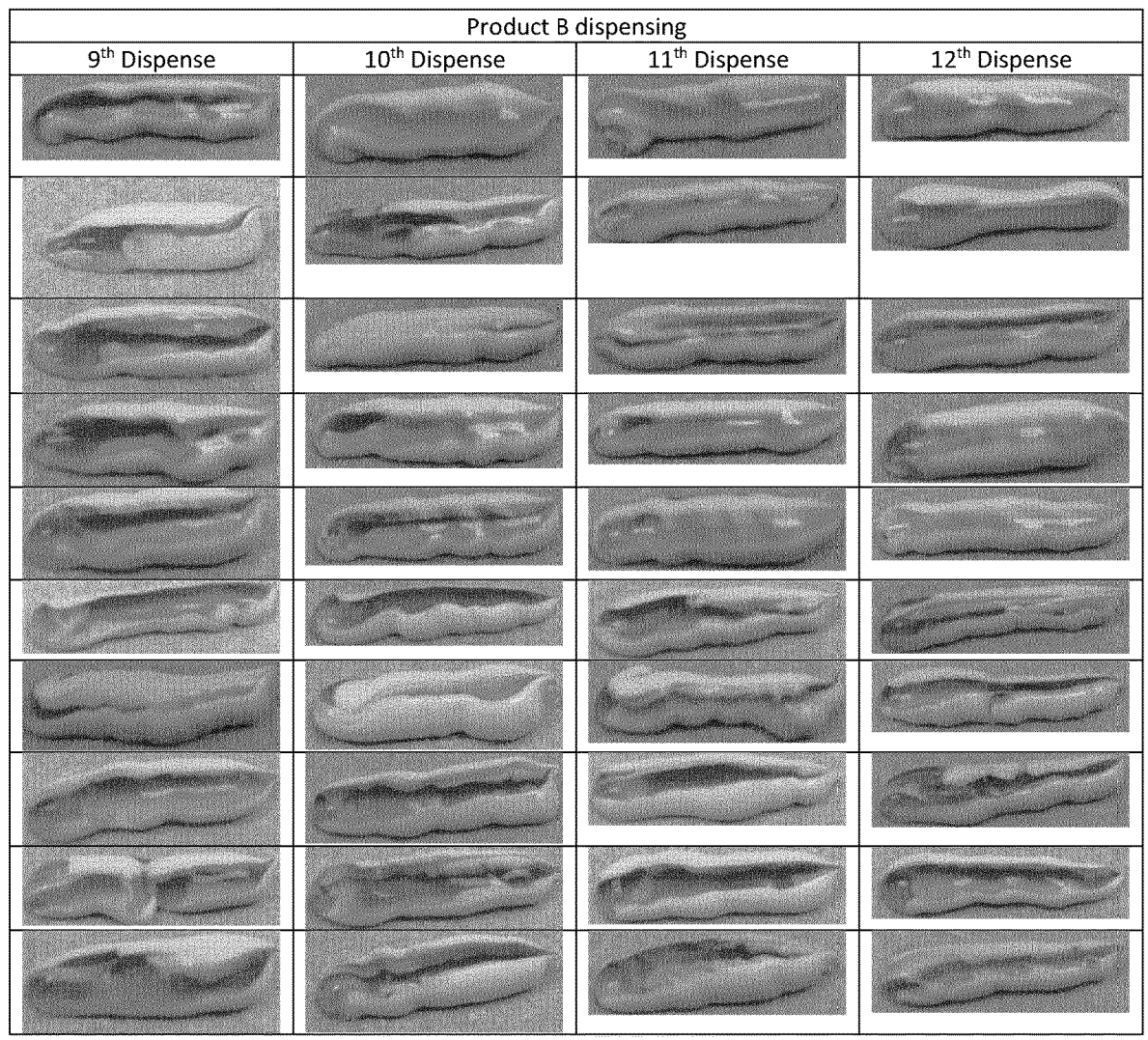
Figure 2D:
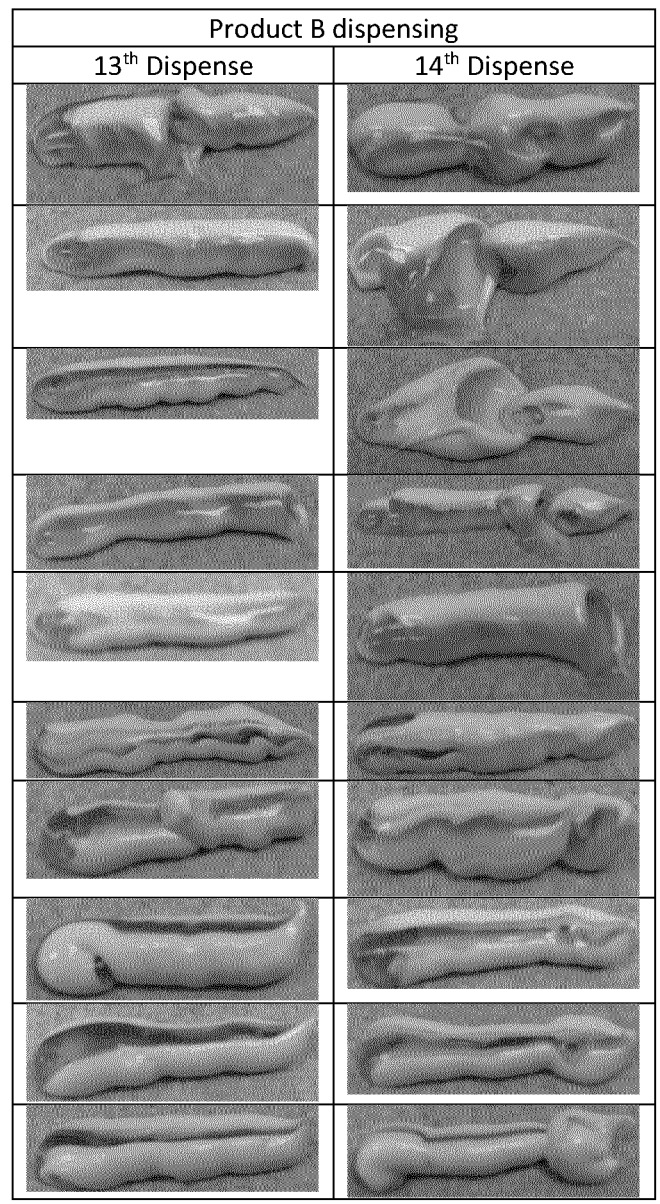
Figure 3A:
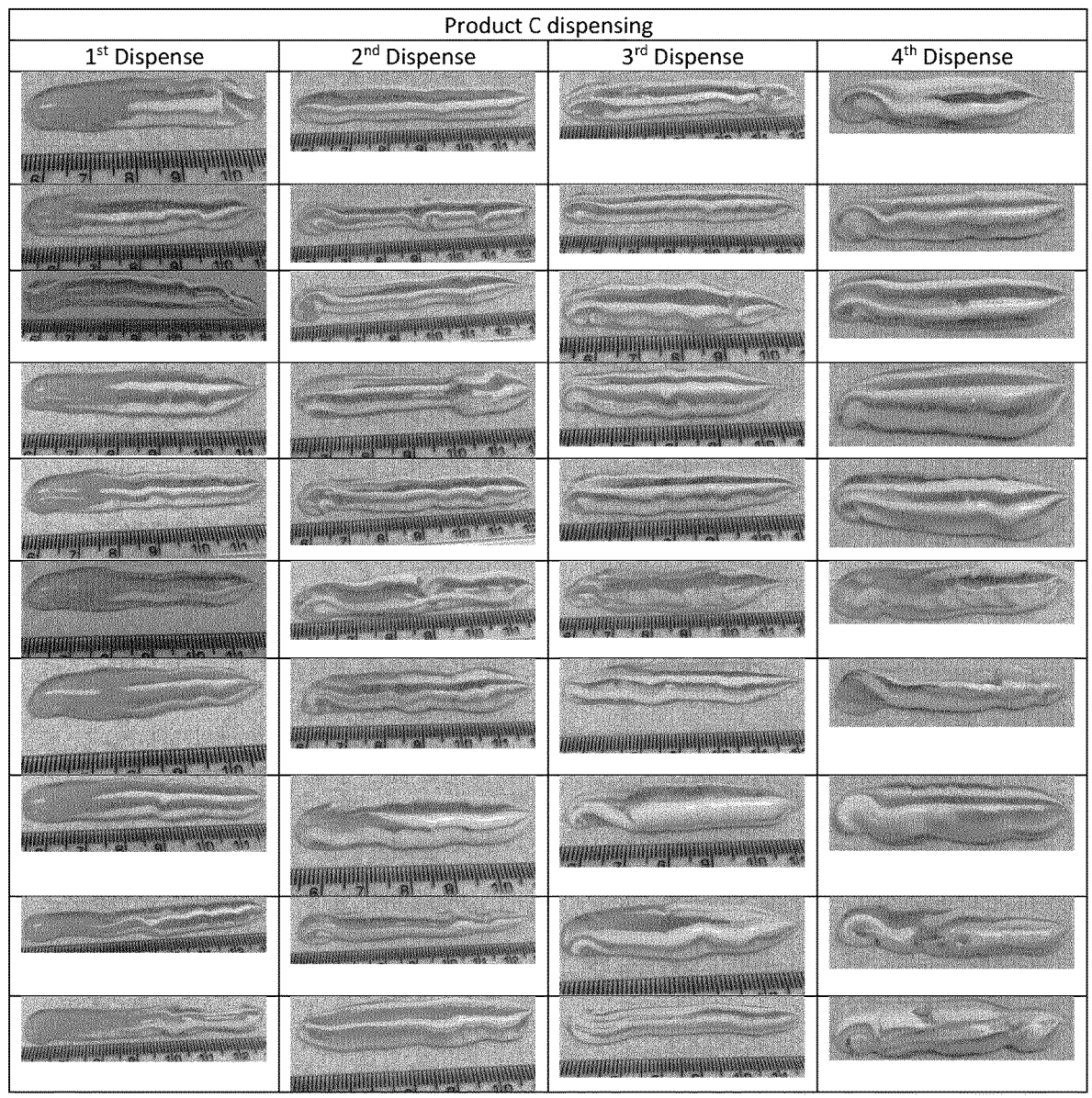
FIG. 3 shows portions of a composition consisting of 20% cream phase as presented in Table 1 and 80% gel phase as presented in Table 2 (Product C) after it is dispensed from a collapsible tube. Fourteen portions of the composition were dispensed from ten tubes at a rate of one portion per day.
Figure 3B:
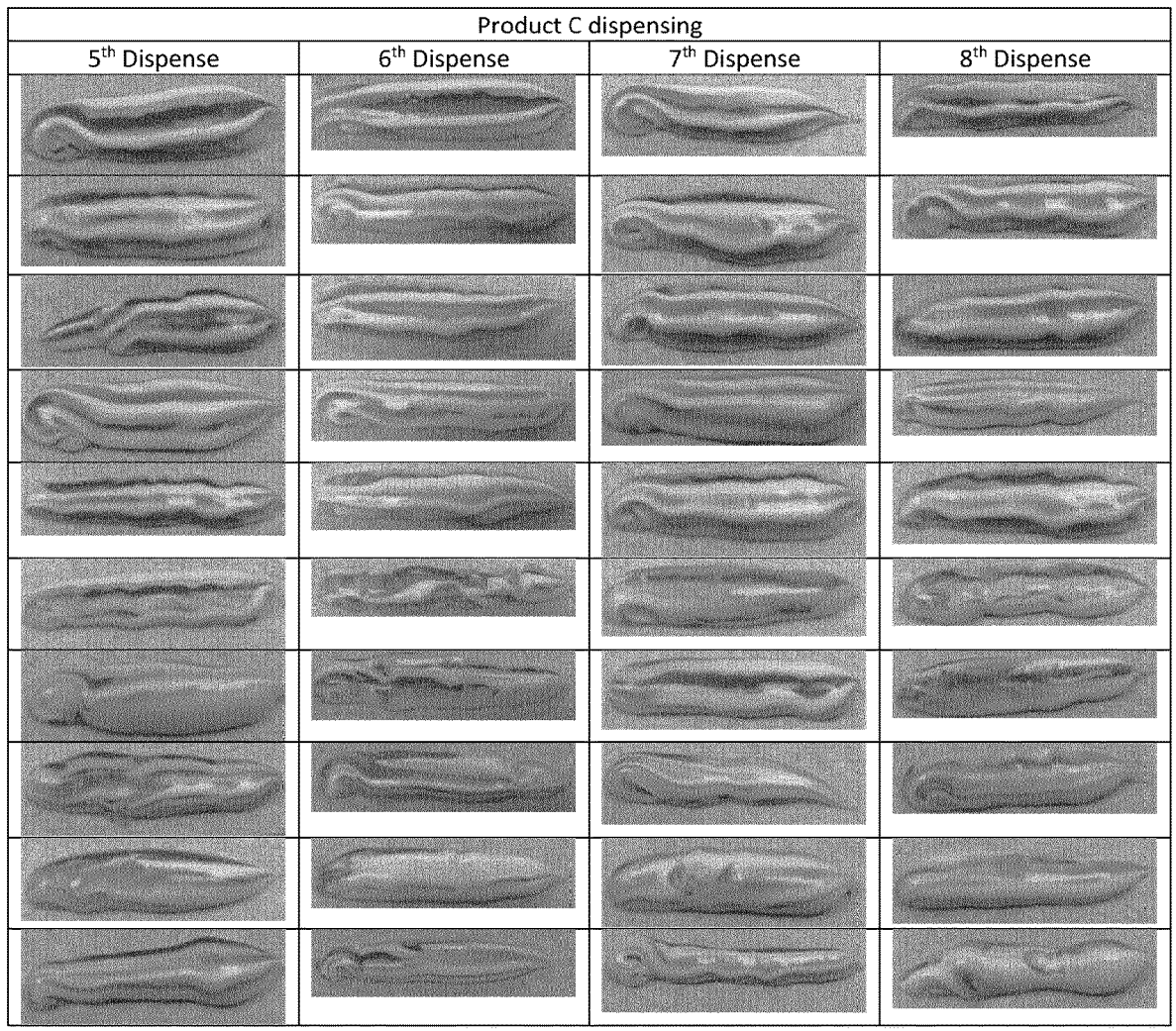
Figure 3C:
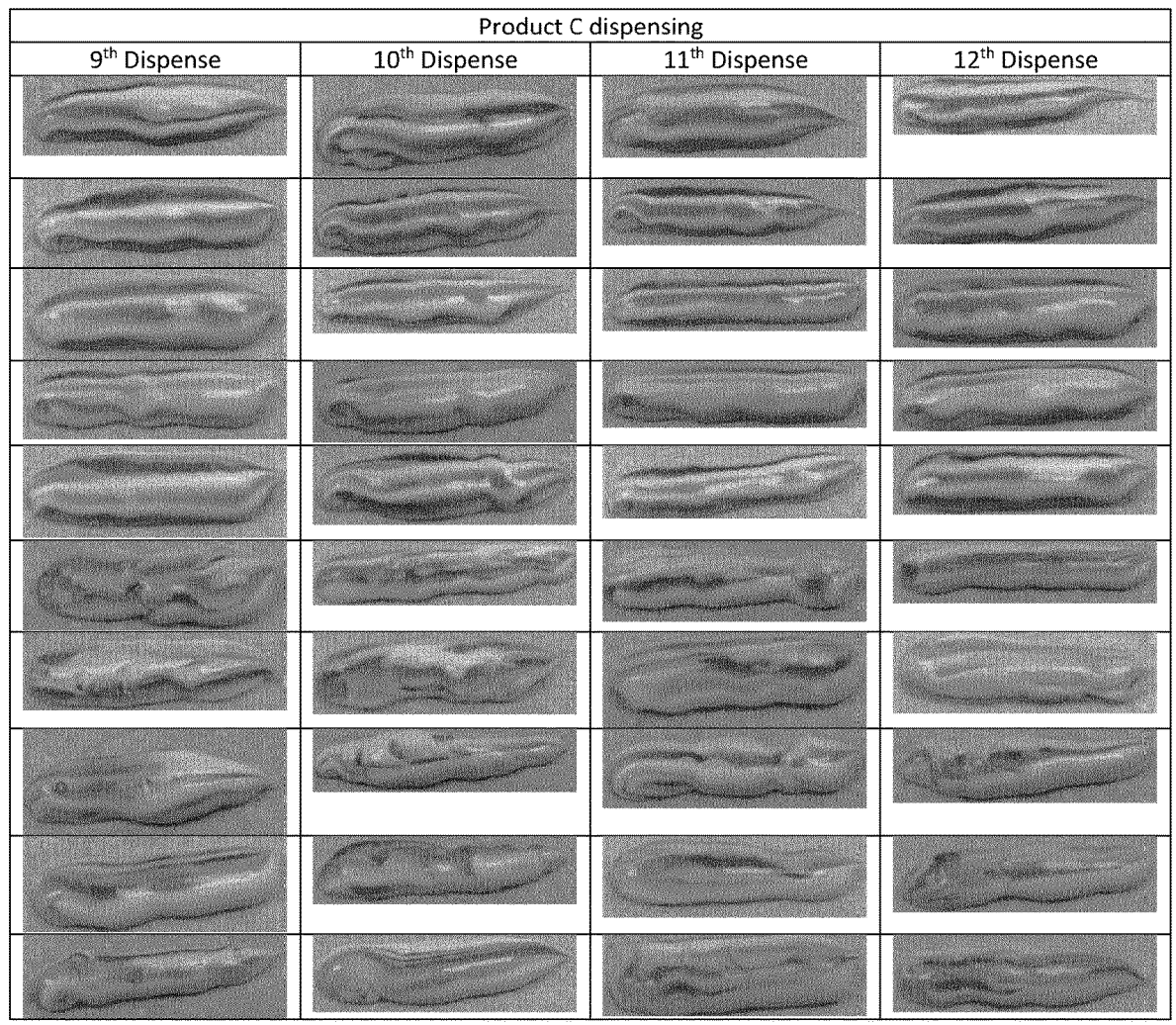
Figure 3D:
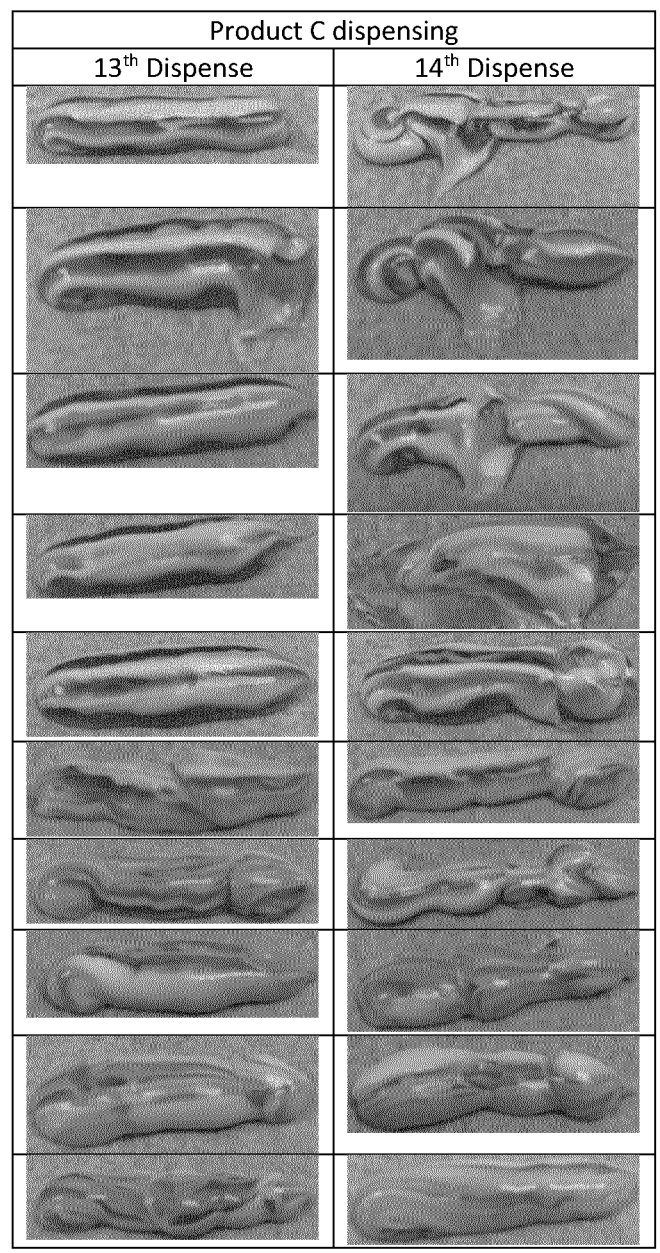

FIGS. 1 to 3 show the images of the dispensed stripes for products A to C respectively. The dark grey sections represent the gel phase, whilst the light grey sections represent the cream phase. By the thirteenth and fourteenth days, the dispensed stripes are not uniform due to the increased difficulty in dispensing the last portions on the product from the tubes.

As seen in FIGS. 2 and 3, products B and C maintain uniform stripes from the first through to the fourteenth dispense. Generally the correct proportions of the cream and gel (50:50 for product B, 20:80 for product C) are present in each dispensed stripe. By contrast, dispensing of product A generally starts with just gel followed by a uniform stripe. This can be seen in the images of FIG. 1 as a dark grey section at the left-hand end of the dispensed stripe. This is thought to be caused by the gel phase flowing more freely than the cream phase in the product A (80% cream, 20% gel) configuration. FIG. 1 also shows that, as a result of this gel end forming, there are occasions upon dispensing that no or very little gel can be seen, suggesting a large level of variation in the proportion of gel obtained with each dispense.

In summary, products B and C maintain uniform stripes from the first through to the fourteenth dispense, with the proportion of the gel and cream with each dispense being largely consistent. By contrast, product A dispensing often leads to a gel-only end, or very little gel at all, resulting in a wide variation in the proportion of gel and cream with each dispense.

Example 5—Transit Testing

In order to assess whether the stripes are maintained after transit from a manufacturing site to a consumer's place of use, sample tubes of Products A, B and C were placed on a shaker for periods of half an hour, two hours or eight hours before dispensing. These simulated conditions are deliberately very severe in order to mimic transit over uneven road surfaces.

FIG. 4 shows images of the dispensed stripes after transit simulation. Products A and B show minimal disruption of the stripes between the cream and gel phases, as distinct stripes are still visible. By contrast, disruption of the stripe of product C took place after just half an hour, with blurring between the phases is evident.

In summary, products A and B produce acceptable stripes after transit and dispensing, whilst product C shows substantial stripe disruption after transit and dispensing.

The invention claimed is:

1. A multi-phase, fluid skincare composition comprising:
   (a) at least one cream phase; and
   (b) at least one gel phase;
   wherein the at least one cream phase and the at least one gel phase are visually distinct phases that are packaged in physical contact;
   wherein a viscosity ratio of a viscosity of the at least one cream phase to a viscosity of the at least one gel phase is from 1:3 to 3:1;
   wherein the viscosity of the at least one cream phase is between 45 Pa·s and 55 Pa·s;
   wherein the viscosity of the at least one gel phase is between 23 Pa·s and 31 Pa·s;
   wherein the at least one cream phase and the at least one gel phase are present in the composition at a level such that a weight ratio of the at least one cream phase to the at least one gel phase is within the range of from 52:48 to 48:52;
   wherein the at least one cream phase is in the form of a water-in-oil and/or silicone emulsion; and wherein the viscosity is measured at 23° C. using a Brookfield RVDV-I Prime viscometer with a heliopath, a speed of 10 revolutions per minute (rpm) for a time of 30 seconds using a T Bar spindle.

2. The composition of claim 1, wherein the composition comprises a bitter substance.

3. The composition of claim 2, wherein the bitter substance is chosen from denatonium compounds, aromatic oils, *eucalyptus* oil, bitter almond oil, menthol, or fruit aroma substances.

4. A collapsible tube having an outlet bore and containing the composition of claim 1, wherein the tube is filled such that, when the composition is extruded from the outlet bore, the extruded composition comprises the at least one cream phase and the at least one gel phase that are visually distinct from one another and within the weight ratio of the at least one cream phase to the at least one gel phase of between 52:48 and 48:52 across the cross-section of the extrusion.

5. The collapsible tube of claim 4, wherein the tube is filled such that, when the composition is extruded from the outlet, the composition forms at least one visually distinct pattern selected from the following patterns: striped, marbled, check, mottled, veined, speckled, ribbons, helical, grooved, ridged, waved, sinusoidal, spiral, contoured, weave or woven, and combinations thereof.

6. A method of moisturising skin, comprising topically applying the composition of claim 1 to the skin.

7. The method of claim 1 comprising topical application to any one or more of the face, the neck skin and/or the décolleté.

8. The composition of claim 1, wherein the at least one cream phase is in the form of a water-in-oil emulsion.

\* \* \* \* \*